US012802817B2

(12) United States Patent
Ce-Ougna et al.

(10) Patent No.: US 12,802,817 B2
(45) Date of Patent: Nov. 17, 2026

(54) CANCER PROGNOSIS

(71) Applicant: Dassault Systemes, Vélizy-Villacoublay (FR)

(72) Inventors: Sarah Ce-Ougna, Vélizy-Villacoublay (FR); Guillaume Lefebvre, Vélizy-Villacoublay (FR); Nicolas Pecuchet, Vélizy-Villacoublay (FR)

(73) Assignee: Dassault Systemes, Vélizy-Villacoublay (FR)

( * ) Notice: Subject to any disclaimer, the term of this patent is extended or adjusted under 35 U.S.C. 154(b) by 608 days.

(21) Appl. No.: 17/821,050

(22) Filed: Aug. 19, 2022

(65) Prior Publication Data

US 2023/0056839 A1 Feb. 23, 2023

(30) Foreign Application Priority Data

Aug. 20, 2021 (EP) .................................... 21306132

(51) Int. Cl.

*G16H 50/20* (2018.01)
*G06T 7/00* (2017.01)
*G16B 40/00* (2019.01)

(52) U.S. Cl.

CPC ........... *G16H 50/20* (2018.01); *G06T 7/0012* (2013.01); *G16B 40/00* (2019.02); *G06T 2207/20084* (2013.01); *G06T 2207/30096* (2013.01)

(58) Field of Classification Search

CPC ...... G16H 50/20; G16B 40/00; G06T 7/0012; G06T 2207/20084; G06T 2207/30096

(Continued)

(56) References Cited

U.S. PATENT DOCUMENTS

| | | | | |
|---|---|---|---|---|
| 10,650,929 B1 | 5/2020 | Beck et al. | | |
| 2007/0168308 A1* | 7/2007 | Wang | ..................... | G16H 70/60 706/924 |

(Continued)

FOREIGN PATENT DOCUMENTS

| | | |
|---|---|---|
| WO | WO 2020/069501 A1 | 4/2020 |
| WO | WO 2021/142209 A1 | 7/2021 |

OTHER PUBLICATIONS

Mobadersany, P., Yousefi, S., Amgad, M., Gutman, D.A., Barnholtz-Sloan, U.S., Vega, J.E.V., Brat, D.J. and Cooper, L.A., 2018. Predicting cancer outcomes from histology and genomics using convolutional networks. Proceedings of the National Academy of Sciences, 115(13), pp. E2970-E2979.

(Continued)

*Primary Examiner* — Stephen S Hong
*Assistant Examiner* — Tionna M Burke
(74) *Attorney, Agent, or Firm* — Oblon, McClelland, Maier & Neustadt, L.L.P.

(57) ABSTRACT

A computer-implemented for parameterizing a statistical function. The statistical function is configured to perform prognosis on cancer patients. The parameterizing method includes obtaining a dataset relative to a plurality of patients each having a cancer disease. The dataset includes, for each patient, input data of the statistical function. The input data include visual data from at least one histological image of a tumor slide of the patient. The input data also include genomic data from sequencing tumor tissue of the patient. The input data further include clinical data of the patient. The dataset also includes clinical endpoints of the patient with respect to evolution of the cancer disease. The parameterizing method further includes parameterizing the statistical function based on the dataset. This forms an improved (Continued)

solution to perform prognosis on patients having a cancer disease.

13 Claims, 10 Drawing Sheets

(58) Field of Classification Search
USPC .......................................................... 382/128
See application file for complete search history.

(56) References Cited

U.S. PATENT DOCUMENTS

| | | | | |
|---|---|---|---|---|
| 2020/0350073 | A1 | 11/2020 | Goldsmith et al. | |
| 2022/0165075 | A1* | 5/2022 | Lee | G06V 10/761 |
| 2023/0207134 | A1* | 6/2023 | Hegde | G06V 10/82 382/133 |

OTHER PUBLICATIONS

Pagès, F., Mlecnik, B., Marliot. F., Bindea, G., Ou, F.S., Bifulco, C., Lugli, A., Zlobec, I., Rau, T.T., Berger, M.D. and Nagtegaal, I.D., 2018. International validation of the consensus Immunoscore for the classification of colon cancer: a prognostic and accuracy study. The Lancet, 391(10135), pp. 2128-2139.
Kather, J.N., Krisam, J., Charoentong, P., Luedde, T., Herpel, E., Weis, C.A., Gaiser, T., Marx, A., Valous, N.A., Ferber, D. and Jansen, L., 2019. Predicting survival from colorectal cancer histology slides using deep learning: A retrospective multicenter study. PLoS medicine, 16(1), p. e1002730.
Saltz, J., Gupta, R., Hou, L., Kurc, T., Singh, P., Nguyen, V., Samaras, D., Shroyer, K.R., Zhao, T., Batiste, R. and Van Arnam, J., 2018. Spatial organization and molecular correlation of tumor-infiltrating lymphocytes using deep learning on pathology images. Cell reports, 23(1), pp. 181-193.
He, K., Gkioxari, G., Dollár, P. and Girshick, R.. 2017. Mask r-cnn. In Proceedings of the IEEE international conference on computer vision (pp. 2961-2969).
Kather, J. N., Suarez-Carmona, M., Charoentong, P., Weis, C. A., Hirsch, D., Bankhead, P., . . . & Schott, S. (2018). Topography of cancer-associated immune cells in human solid tumors. Elife, 7, e36967.
Corredor, G., Wang, X., Zhou, Y., Lu, C., Fu, P., Syrigos, K., . . . & Velcheti, V. (2019). Spatial architecture and arrangement of tumor-infiltrating lymphocytes for predicting likelihood of recurrence in early-stage non-small cell lung cancer. Clinical cancer research. 25(5), 1526-1534.
Heindl, A., Sestak, I., Naidoo, K., Cuzick, J., Dowsett, M., & Yuan, Y. (2018). Relevance of spatial heterogeneity of immune infiltration for predicting risk of recurrence after endocrine therapy of ER+ breast cancer. JNCI: Journal of the National Cancer Institute, 110(2), 166-175.
Jackson, H.W., Fischer, J.R., Zanotelli, V.R., Ali, H.R., Mechera, R., Soysal, S.D., Moch, H., Muenst, S., Varga, Z., Weber, W.P. and Bodenmiller, B., 2020. The single-cell pathology landscape of breast cancer. Nature, 578(7796), pp. 615-620.
Yuan, Y., 2016. Spatial heterogeneity in the tumor microenvironment. Cold Spring Harbor perspectives in medicine, 6(8), p. a026583.
Yuan et al. 2012. Quantitative image analysis of cellular heterogeneity in breast tumors complements genomic profiling. Science translational medicine, 4(157), pp. 157ra143-157ra143.
Becht, E & al., 2016. Estimating the population abundance of tissue-infiltrating immune and stromal cell populations using gene expression. Genome biology, 17(1), pp. 1-20.
Zhu, X., Yao, J. and Huang, J., 2016, December. Deep convolutional neural network for survival analysis with pathological images. In 2016 IEEE International Conference on Bioinformatics and Biomedicine (BIBM) (pp. 544-547). IEEE.
The extended European search report mailed Feb. 16, 2022 in corresponding European Patent Application No. 21306132.8 (11 pages).
Abduljabbar K et al: “Geospatial immune variability illuminates differential evolution of lung adenocarcinoma”, Nature Medicine, Nature Publishing Group US, New York, vol. 26, No. 7, May 27, 2020.
Office Action dated Sep. 1, 2026, issued in counterpart JP Application No. 2022-129077, citing documents No. 1-4, with English Translation. (27 pages).

* cited by examiner

CANCER PROGNOSIS

CROSS-REFERENCE TO RELATED APPLICATIONS

This application claims priority under 35 U.S.C. § 119 or 365 to European Application No. 21306132.8, filed Aug. 20, 2021. The entire contents of the above application are incorporated herein by reference.

TECHNICAL FIELD

The disclosure relates to the field of data science applied in medicine, and more specifically to methods, data structures and systems related to performing prognosis on cancer patients.

BACKGROUND

Data science is gaining wide importance in the medical field, where data increasingly available on patients can be used to perform medical assessments on those patients more and more accurately. In this context, solutions have been proposed to perform prognosis on cancer patients. Such solutions allow modulating treatment of those patients and thereby increase their chances of recovery.

Existing solutions for performing prognosis on patients having a cancer disease are most often based on medical images of the patients. A famous example known as the "ImmunoScore" is disclosed in the following paper:

Pagès, F., Mlecnik, B., Marliot, F., Bindea, G., Ou, F. S., Bifulco, C., Lugli, A., Zlobec, I., Rau, T. T., Berger, M. D. and Nagtegaal, I. D., 2018. International validation of the consensus Immunoscore for the classification of colon cancer: a prognostic and accuracy study. *The Lancet,* 391(10135), pp.2128-2139.

The following papers also relate to this field and are referred to hereinafter:

Kather, J. N., Krisam, J., Charoentong, P., Luedde, T., Herpel, E., Weis, C. A., Gaiser, T., Marx, A., Valous, N. A., Ferber, D. and Jansen, L., 2019. Predicting survival from colorectal cancer histology slides using deep learning: A retrospective multicenter study. *PLoS medicine,* 16(1), p.e1002730.

Saltz, J., Gupta, R., Hou, L., Kurc, T., Singh, P., Nguyen, V., Samaras, D., Shroyer, K. R., Zhao, T., Batiste, R. and Van Arnam, J., 2018. Spatial organization and molecular correlation of tumor-infiltrating lymphocytes using deep learning on pathology images. *Cell reports,* 23(1), pp.181-193.

He, K., Gkioxari, G., Dollár, P. and Girshick, R., 2017. Mask r-cnn. In Proceedings of the *IEEE international conference on computer vision* (pp. 2961-2969).

Kather, J. N., Suarez-Carmona, M., Charoentong, P., Weis, C. A., Hirsch, D., Bankhead, P., . . . & Schott, S. (2018). Topography of cancer-associated immune cells in human solid tumors. *Elife,* 7, e36967.

Corredor, G., Wang, X., Zhou, Y., Lu, C., Fu, P., Syrigos, K., . . . & Velcheti, V. (2019). Spatial architecture and arrangement of tumor-infiltrating lymphocytes for predicting likelihood of recurrence in early-stage non-small cell lung cancer. *Clinical cancer research,* 25(5), 1526-1534.

Heindl, A., Sestak, I., Naidoo, K., Cuzick, J., Dowsett, M., & Yuan, Y. (2018). Relevance of spatial heterogeneity of immune infiltration for predicting risk of recurrence after endocrine therapy of ER+ breast cancer. *JNCI: Journal of the National Cancer Institute,* 110(2), 166-175.

Jackson, H. W., Fischer, J. R., Zanotelli, V. R., Ali, H. R., Mechera, R., Soysal, S. D., Moch, H., Muenst, S., Varga, Z., Weber, W. P. and Bodenmiller, B., 2020. The single-cell pathology landscape of breast cancer. *Nature,* 578(7796), pp.615-620.

Yuan, Y., 2016. Spatial heterogeneity in the tumor microenvironment. *Cold Spring Harbor perspectives in medicine,* 6(8), p.a026583.

Yuan & al. 2012. Quantitative image analysis of cellular heterogeneity in breast tumors complements genomic profiling. *Science translational medicine,* 4(157), pp.157ra143-157ra143.

Becht, E & al., 2016. Estimating the population abundance of tissue-infiltrating immune and stromal cell populations using gene expression. *Genome biology,* 17(1), pp.1-20.

Zhu, X., Yao, J. and Huang, J., 2016, December. Deep convolutional neural network for survival analysis with pathological images. In 2016 *IEEE International Conference on Bioinformatics and Biomedicine* (*BIBM*) (pp. 544-547). IEEE.

Existing solutions, in particular the ImmunoScore, present a few drawbacks. They are based only on local subarea analysis, and thus do not fully use the complete data present in the medical images of the patient. They also require a predetermined value, often a threshold, of which estimation includes some heuristics. In addition, they do not exploit other data available on the patient than the medical images.

There is thus a need to provide a computer-implemented solution to perform prognosis on patients having a cancer disease with higher accuracy.

SUMMARY

It is therefore provided a computer-implemented for parameterizing a statistical function, hereinafter referred to as the "parameterizing method". The statistical function is configured for performing prognosis on cancer patients. The parameterizing method comprises providing a dataset relative to a plurality of patients each having a cancer disease. The dataset includes, for each patient, input data of the statistical function. The input data comprise visual data from at least one histological image of a tumor slide of the patient. The input data also comprise genomic data from sequencing tumor tissue of the patient. The input data further comprise clinical data of the patient. The dataset also includes clinical endpoints of the patient with respect to evolution of the cancer disease. The parameterizing method further comprises parameterizing the statistical function based on the dataset.

The parameterizing method may comprise one or more of the following:

- the visual data are obtained from one or more maps representing one or more distributions including: a distribution of tissue textures, a distribution of lymphocyte presence, and/or a distribution of cell density;
- at least one map is extracted from the at least one histological image via a respective convolutional neural network;
- the one or more maps comprise several maps each representing a respective distribution;
- the one or more maps comprise a texture map extracted from the at least one histological image via a first CNN, the texture map having pixels each representing a texture among a predetermined set of textures, each pixel resulting from classifying a respective tile of the at least one histological image with the first CNN;

the one or more maps comprise a lymphocyte map extracted from the at least one histological image via a second CNN, the lymphocyte map having pixels each indicative of lymphocyte presence, each pixel resulting from classifying a respective tile of the at least one histological image with the second CNN;

the one or more maps comprise a cell density map extracted from the at least one histological image via a third CNN, the cell density map having pixels each representing a local number of cells, each pixel resulting from counting a number of cells in a respective tile of the at least one histological image with the third CNN;

the genomic data represent a cell-type distribution and/or gene expression data;

the clinical data represent at least one among patient age, patient gender, tumor stage, lymph node stage and/or metastasis stage;

the statistical function comprises a neural network, a stochastic model, and/or a regression model such as a Cox model; and/or the statistical function is configured to output a prediction on patient's outcome and/or a prediction on tumor evolution.

It is also provided a computer-implemented of use of a statistical function parameterized with the parameterizing method, for performing prognosis on a cancer patient, hereinafter referred to as the "use method". The use method comprises providing input data. The input data include visual data from at least one histological image of a tumor slide of the patient, genomic data from sequencing tumor tissue of the patient, and clinical data of the patient. The use method also comprises applying the statistical function to the input data to perform prognosis on the patient.

It is also provided a computer-implemented for forming the dataset of the parameterizing method, hereinafter referred to as the "dataset-forming method". In other words, the dataset obtained by the dataset-forming method is configured to be provided as such in the parameterizing method, so as to parameterize the function based on said dataset. In the dataset, the input data are related to the clinical endpoints patient-wise, meaning that for each patient, the dataset is structured such that the input data for the patient can be associated with the clinical endpoints of the patient. This may be implemented via a relation in a relational database or both input data and clinical endpoints belonging to a same table, via data pointers from/to both input data/clinical endpoints, or yet via patient IDs being appended to both input data and clinical endpoints.

It is further provided a data structure related to the above methods, in other words, data tangibly recorded on a data storage medium, for example via one or more data files. The data structure comprises any one or any combination of the following:

a statistical function parameterized according to the parameterizing method (in other words, the data structure represents the statistical function), a dataset formed according to the dataset-forming method, and/or a computer program comprising instructions for performing the parameterizing method, the use method, and/or the dataset-forming (when the instructions are executed by a processor of a computer system).

It is further provided a device comprising a data storage medium having recorded thereon the data structure.

The device may form or serve as a non-transitory computer-readable medium, for example on a SaaS (Software as a service) or other server, or a cloud based platform, or the like. The device may alternatively comprise a processor coupled to the data storage medium. The device may thus form a computer system in whole or in part (e.g., the device is a subsystem of the overall system). The system may further comprise a graphical user interface coupled to the processor.

BRIEF DESCRIPTION OF THE DRAWINGS

Non-limiting examples will now be described in reference to the accompanying drawings, where.

DETAILED DESCRIPTION

Figure 1:
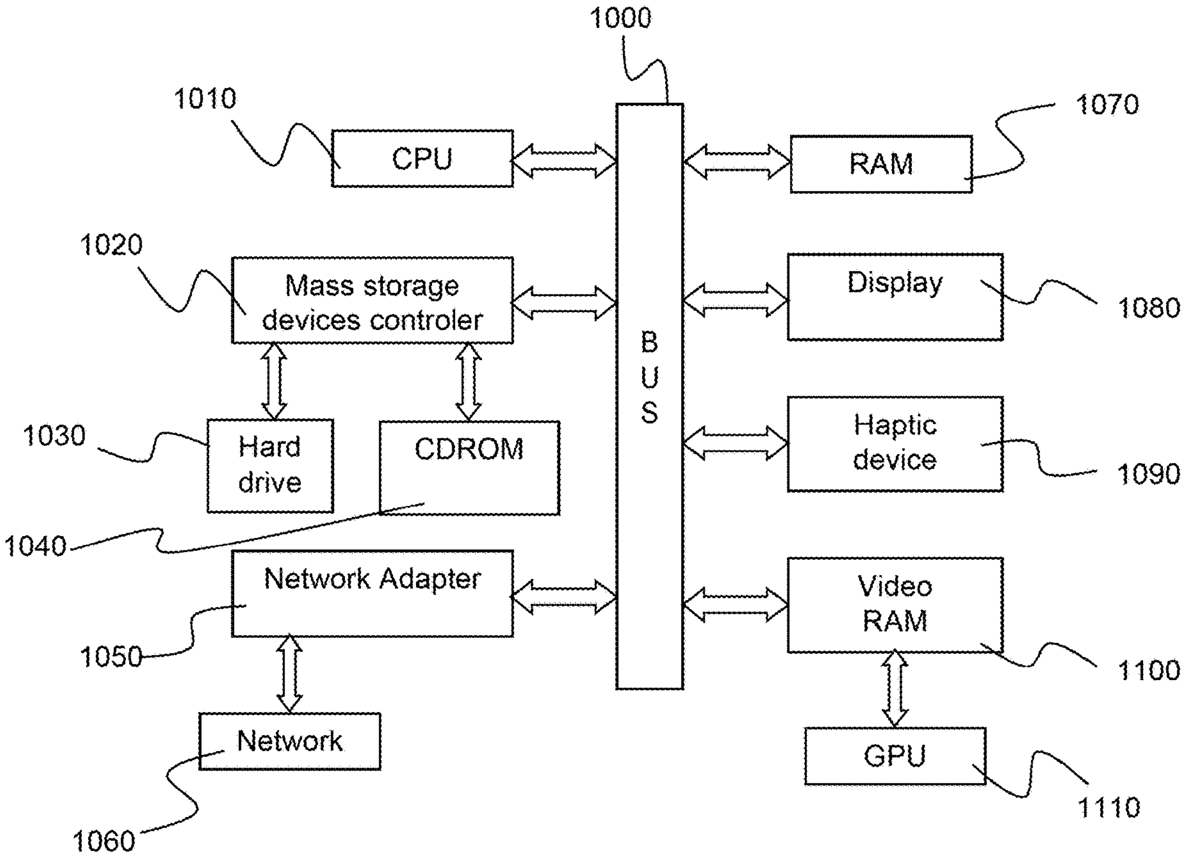
FIG. 1 shows an example of the system.

The parameterizing method may include the dataset-forming method. In other words, the dataset-providing step in the parameterizing method may implement the dataset-forming method. Thus, when in the following it is referred to examples of obtaining data pieces of the dataset, these examples may apply to any one or both the dataset-providing step of the parameterizing method and the dataset-forming method. In addition, when these data pieces are part of the input data of the statistical function, these examples may further apply to the use method, where such input data are also provided. In other words, providing the input data in the use method may be performed similarly to providing the input data in the parameterizing method and/or in the dataset-forming method. In particular, in examples where the statistical function takes as input clinical data in addition to the visual data and the genomic data, and thus the dataset comprises such clinical data, the use method may also comprise providing clinical data of the patient among the input data.

The methods presented herein are all part of a global solution for performing prognosis on patients having a cancer disease. The dataset-forming method allows obtaining a dataset that can be used in the parameterizing method. The parameterizing method allows to parameterize a statistical function that can be used in the use method. In turn, the use method allows to perform prognosis on a patient having the cancer disease.

The proposed solution allows to perform prognosis on patients having a cancer disease with higher accuracy.

The dataset relates/associates medical data of patients each having a cancer disease with known clinical endpoints of those patients, that is, real outcome of the cancer disease for those patients. The dataset can thus serve to parameterize a function adapted in the use method to perform a statistical prognosis, that is, to statistically infer outcome of the cancer disease of new patients, when the same type of medical data are provided but the clinical endpoints are not known yet.

The medical data comprise, patient-wise, not only visual data from at least one histological image of a tumor slide, but also genomic data from sequencing tumor tissue and clinical data. Thus, the prognosis is based on a combination of visual data, genomic data, and clinical data. The combination of visual data with genomic data and clinical data improves accuracy of the prognosis. The visual data provide spatial information on the tumor, such as on co-existence of different tissues inside the tumor (for example information on whether immune cells are present in a diffuse manner in the tumor or rather isolated only in a sub-part of the tumor). The genomic data provide functional information, such as on the activation state of the different cells in the tumor (for example, information on whether the immune cells are exhausted lymphocytes, active lymphocytes, or macrophages). Such combination of spatial information and functional information forms a relatively comprehensive picture of the state of the cancer in a patient, thus allowing improved prognosis. The clinical data further improve the parameterizing, by providing medical context to the biological/measurement data (visual and genomic data).

The visual data may represent the tumor slide in its entirety, such that the statistical function does not perform local subarea analysis and rather fully uses the complete data present in the at least one histological image. Alternatively or additionally, the parameterizing of the statistical function may be fully automatic once the dataset is provided, such that no heuristics need be implemented to define a predetermined value such as a threshold. In other words, the parameterizing method may be repeated on different datasets without any specific user-setting between the repetitions. These options yet improve the prognosis and/or ergonomics.

The methods are computer-implemented. This means that steps (or substantially all the steps) of each method are executed by at least one computer, or any system alike. Thus, steps of the methods are performed by the computer, possibly fully automatically, or, semi-automatically. In examples, the triggering of at least some of the steps may be performed through user-computer interaction. The level of user-computer interaction required may depend on the level of automatism foreseen and put in balance with the need to implement user's wishes. In examples, this level may be user-defined and/or pre-defined.

A typical example of computer-implementation of a method is to perform the method with a system adapted for this purpose. The system may comprise a processor coupled to a memory and a graphical user interface (GUI), the memory having recorded thereon a computer program comprising instructions for performing the method. The memory may also store a database. The memory is any hardware adapted for such storage, possibly comprising several physical distinct parts (e.g., one for the program, and possibly one for the database).

FIG. 1 shows an example of the system, wherein the system is a client computer system.

The client computer of the example comprises a central processing unit (CPU) 1010 connected to an internal communication BUS 1000, a random access memory (RAM) 1070 also connected to the BUS. The client computer is further provided with a graphical processing unit (GPU) 1110 which is associated with a video random access memory 1100 connected to the BUS. Video RAM 1110 is also known in the art as frame buffer. A mass storage device controller 1020 manages accesses to a mass memory device, such as hard drive 1030. Mass memory devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks 1040. Any of the foregoing may be supplemented by, or incorporated in, specially designed ASICs (application-specific integrated circuits). A network adapter 1050 manages accesses to a network 1060, for example so as to access remote data (the dataset may indeed be stored on local memory such as hard drive 1030, and/or on distant memory such as a cloud). The client computer may also include a haptic device 1090 such as cursor control device, a keyboard or the like. A cursor control device is used in the client computer to permit the user to selectively position a cursor at any desired location on display 1080. In addition, the cursor control device allows the user to select various commands, and input control signals. The cursor control device includes a number of signal generation devices for input control signals to system. Typically, a cursor control device may be a mouse, the button of the mouse being used to generate the signals. Alternatively or additionally, the client computer system may comprise a sensitive pad, and/or a sensitive screen.

The computer program may comprise instructions executable by a computer, the instructions comprising means for causing the above system to perform any method herein. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the method.

The statistical function is configured for performing prognosis on patients having a cancer disease. In other words, the statistical function is configured to output patient-wise information relative to patient's future with respect to the cancer disease of the patient. The statistical function may for example be configured to output a prediction on patient's outcome. The prediction on patient's outcome may comprise a risk score, for example measuring a risk of death and/or relapse of a patient, and/or a risk of survival. For example, the risk or survival score may consist of a scalar factor to be applied to a predetermined value for the general population. Additionally or alternatively, the statistical function may be configured to output a prediction on tumor evolution, for example relative to size growth, shape evolution, affected organs, and/or type of tumor cells. The output information may apply to a predetermined time duration. For example, the risk score may represent a risk of death and/or relapse within said time duration, or alternatively a risk of survival within said time duration. As another example, the statistical function may output information representing tumor evolution for said time duration. Alternatively, the output information may comprise a variable probability of outcomes at different time points. For example, the output information may comprise an estimated probability of survival at different time points, or an estimated probability of global degradation of patient's conditions at different time points, or an estimated probability of tumor response (defined by tumor size staying below a predetermined size such as the size at the time of diagnosis) at different time points, estimated probability for the tumor to double in size at different time points. Further alternatively or additionally, the statistical function may be configured for outputting one or more treatments (e.g., an optimal treatment for the patient). Yet alternatively or additionally, the statistical function may be configured to output a conditional prediction on patient's outcome and/or a prediction on tumor evolution (such as any combination of the above-listed examples), for example a prediction which assumes that the patient follows one or more treatments (e.g., such as treatment outputted by the statistical function itself).

The use method may comprise displaying information depending on the output of the statistical function, on a computer system graphical user interface. For example, the use method may comprise displaying a graphical representation of the output, such as a textual representation, a chart, a table, or a visual animation (e.g., of patient outcome probability throughout time or tumor evolution throughout time). The use method may comprise providing tools in the graphical user interface to modify the display and/or access the statistical function's input and display a graphical representation of such input. The user, e.g., a medical practitioner or a pharmaceutical and/or medical researcher or biologist, may thus visualize the output prognosis of the statistical method and also the corresponding input data of the patient.

The use method may further comprise determining a treatment (patient not yet treated for the cancer disease) or a treatment adaptation (patient already being treated for the cancer disease) based on the output prognosis. For instance, the use method may determine the nature and intensity of peri-surgical or adjuvant therapies. Additionally or alternatively, the method may determine a follow-up visit (e.g., the method may comprise prescribing a time and/or nature of such a follow-up visit), and/or a surveillance with diagnostic tests (e.g., the method may comprise prescribing a time and/or nature of such diagnostic tests).

Any patient herein is a cancer patient, i.e., affected by a cancer disease. The patients of the dataset may all be affected by the same type of cancer disease, such that the statistical function is specialized, and such that the use method may rather be applied for a patient also affected by the same type of cancer disease. Alternatively, different patients of the dataset may be affected by different types of cancer diseases, such that the statistical function is generic.

Any cancer disease herein may be of any type, such as a breast cancer, a colorectal cancer, a bladder cancer, a kidney cancer, a lung cancer, a lymphoma, a melanoma, an oral and/or oropharyngeal cancer, a pancreatic cancer, a prostate cancer, a thyroid cancer, a uterine cancer, an ovarian cancer. Any patient herein may be at any stage of a cancer disease.

The statistical function is configured to process patient-wise input data so as to statistically infer a prognosis depending on such input data. Such statistical functions are well-known in the field of computer-implemented solutions applied to medicine. The statistical function may for example comprise or consist of a neural network. With the explosion of available computational resources, neural networks are increasingly being used in the field of medical science to perform assessments based on patients' medical data, and they have proved to be effective in finding correlations between input and output even when the correlation is non-linear. Neural networks can thus be parameterized based on ground truth inputs associated with ground truth outputs, and in an agnostic manner with respect to input-output correlation. Alternatively or additionally, the statistical function may comprise a regression model, such as a Cox model. Yet alternatively or additionally, the statistical function may comprise a stochastic model. Such models are also widely used in medicine and in particular in data science applied to prognosis.

By "parameterizing" the statistical function, it is meant determining/setting values of the coefficients (i.e., parameters) of the function. This is performed by the parameterizing method based on the dataset, by finding values that patient-wise perform predictions that best approach (globally on the dataset) the clinical endpoints known from the input data. In case the statistical function comprises a neural network, the parameterizing method amounts to a machine-learning method. In such as case, the parameterizing step amounts to a training step that consists in varying weights and/or biases of the neural network, and where the dataset provides patient-wise training samples/examples each comprising respective (ground truth) input data associated to (ground truth) clinical endpoints. In case the statistical function comprises a regression model or a stochastic model, the parameterizing step amounts to setting the model's coefficients in consistency with the dataset seen as a statistical sample. In all cases, the parameterizing step (e.g., training) may comprise an optimization that forces the statistical function to output values consistent with the dataset, e.g., by minimizing a predetermined loss which measures a disparity (e.g., a likelihood term) between the output of the function when applied to the ground truth input data, and the ground truth clinical endpoints.

The clinical endpoints may comprise any type of data representing patient-wise outcome of the patient's cancer disease. The clinical endpoints may comprise evolution data, including for example information relative to patient's survival, death, or relapse, and/or information on tumor size evolution. The information in the clinical endpoints may be dated or undated. The clinical endpoints may for example consist of overall survival in months, and overall survival status (living or deceased).

The input data of the statistical function are now discussed.

The genomic data consist of data obtained from sequencing tumor tissue of the patient. In other words, any method herein may comprise sampling tissue of a tumor of a given patient (via a biopsy or surgical resection), and sequencing genome of such tissue (e.g., with an RNA or DNA sequencing machine). The tumor may be the primary tumor of the cancer disease of the patient. The genomic data may comprise or consist of any final or intermediary result of the sequencing, or any post-processing of such result. For example, the genomic data may indicate (i.e., represent directly or indirectly) a cell-type distribution (e.g., a score of different cell types in the sampled tissue) and/or gene expression data (e.g., a list of reference genes and a respective level of expression associated to each gene, for example expressed in Fragments Per Kilobase of transcript per Million mapped reads or FPKM). The genomic data may comprise or allow retrieving functional information on the immune response of the patient against the tumor, for example including a distribution of immune cell-types among types including exhausted lymphocytes, active lymphocytes, and/or macrophages, and/or information on the cancer disease of the patient, for example including a number of mutations and/or one or more mutation types. The genomic data may be in the form of textual data and/or numeric data (i.e., numbers and/or vectors of numbers) derived from such textual data.

In an example, any method herein may comprise determining the genomic data as a vector of scores, each score being a number representing a relative quantity (or "population")—in the sampled tissue—of a respective cell-type among a predetermined set of cell-types. The predetermined set of cell-types may be a set of cell-types of interest relevant to the cancer disease, and/or including immune cell-types. The predetermined set of cell-types may include any combination of the following types: T cells, CD8 T cells, cytotoxic lymphocytes, B lineage, NK cells, monocytic lineage, myeloid dendritic cells, neutrophils, endothelial cells, and fibroblasts. Optionally, each score may be a function (e.g., log2 function, also referred to as "binary logarithm" function) of a genetic expression quantity associated to the respective cell-type. Further optionally, the respective cell-type may be associated to a respective set of one or more genes, and a level of expression of each gene may be retrieved from the sequencing, the individual level of expression(s) of the one or more genes being combined so as to form the genetic expression quantity. Yet optionally, the combination may comprise or consist in a geometric mean of said individual level(s) of gene expression.

The clinical data consist of data collected in the course of patient care, such as though interrogating the patient and/or performing diagnosis on the patient. The clinical data may be in the form of textual data and/or numeric data (i.e., numbers and/or vectors of numbers) derived from such textual data. The clinical data may represent at least one among patient age, patient gender, tumor stage, lymph node stage, and/or metastasis stage. For example the clinical data may comprise patient age, patient gender, tumor stage, lymph node stage, and metastasis stage. The clinical data may optionally further represent any one or any combination of the following information: tumor stage from 1 to 4 (i.e., increasing level), lymph node stage from 0 to 2 (i.e., increasing level), metastasis stage which is either 0 or 1 (i.e., respectively indicating presence or absence of metastasis), cancer type (e.g., mucinous or not), primary tumor site (e.g., in the case of a colorectal cancer, cecum, ascending colon, hepatic flexure, transverse colon, splenic flexure, descending colon, sigmoid, recto-sigmoid or rectum), lymphovascular invasion (yes or no, e.g., 1 or 0), vascular invasion (yes or no, e.g., 1 or 0), MSI/MSS sensor score, neo-adjuvant therapy administered prior to tumor resection (yes or no, e.g., 1 or 0).

The visual data are obtained from at least one histological image of a tumor slide of the patient (a single histological image or several such images). The tumor may be the primary tumor of the cancer disease of the patient. The visual data are said to be "visual" as they directly stem from at least one image. The visual data may comprise one or more images. Additionally or alternatively, the visual data may comprise any type of information (e.g., features) extracted from one or more images and optionally discard said images (i.e., the visual data comprise no image). Any method herein may comprise capturing (or retrieving from memory) at least one histological image of a tumor slide of the patient.

Histological images (also referred to as "histology images") are (magnified) microscopic images of patient tissue, also called "histopathological" or "histo-pathological" images when performed on tissue affected by a disease, such as tumor tissue. The at least one histological image may be captured with any adapted imaging device, such as a microscopic imaging device. For example, any method herein may comprise performing a tumor biopsy or surgical resection to provide a tumor sample (tumor tissue block), cutting the tumor sample in thin slices or layers, and capture an image with a high microscopic magnification. The tumor layers may be placed on a glass slide before the capturing. The expression "tumor slide" designates the portion of the glass slide covered with tumor tissue. The tumor tissue on the slide may present an area of at least 0.1 $cm^2$, 0.5 $cm^2$, or 1 $cm^2$. For example, the tumor tissue may cover a zone of at least 1 $cm^2$ of the glass slide. The microscope magnification may be at least a 5× magnification or yet a 10× magnification, for example a 20× magnification (0.50 μm/pixel) or a 40× magnification (0.25 μm/pixel). Therefore the 1 $cm^2$ tumor tissue corresponds to 400 million px (pixels) at 40× magnification or 200 million px at 20× magnification.

The at least one histological image may (e.g., each) be a non-immuno-stained histopathological image (i.e., not processed by immuno-staining). Rather, the at least one histological image may (e.g., each) be a hematoxylin-eosin-safran (HES) (e.g., unimmunized) stained slide.

Any method herein may comprise re-defining (i.e., re-sizing) the at least one histological image to remove background and keep substantially only pixels of the at least one histological image representing tumor tissue. For example, at least 90% or 95% of the pixels of the re-defined histological image (i.e., the at least one image resulting from the re-defining) may each represent tumor tissue. In addition, the re-defining may keep substantially all the part of the at least one histological image representing tumor tissue. For example, at least 95% or 99% of the pixels of the initial at least one histological image each representing tumor tissue may also be present in the re-defined at least one histological image. The re-defining may comprise or consist of trimming the at least one histological image so as to remove background surrounding the representation of tumor tissue (in the center of the initial image), for example by determining a bounding box of represented tumor tissue and removing portions outside the bounding box (thus representing the background). The re-defining may comprise a thresholding algorithm to identify portions of the glass slide not covered by tumor tissue.

The visual data may comprise or consist of the at least one histological image or the re-defined histological image (e.g., in whole). Alternatively or additionally, any method herein may comprise processing the at least one histological image or the re-defined histological image (e.g., in whole, that is, everywhere) to extract another type of visual data. The following discussion of such processing applies the at least one histological image, after or without the optional re-defining.

In particular, the visual data may be obtained from one or more maps (or "masks") representing one or more attribute distributions (i.e., a distribution of an attribute over the at least one histological image). The processing of the at least one histological image may comprise extracting such one or more maps from the least one histological image.

The at least one histological image may be a very high resolution color (e.g., RGB) image of a relatively small tissue sample. For example, the at least one histological image may represent a tumor slide having an area lower than 10 $cm^2$ or 5 $cm^2$. Additionally or alternatively, the at least one histological image may contain more than 10 million, 50 million, or even 100 million pixels covering the tumor slide (that is, pixels covering the zone of the glass side covered by tumor tissue, e.g., regularly spread over the tumor slide). For example, the re-defined tumor slide may consist substantially (for at least 90% of its area) of tissue area and may cover at least 1 $cm^2$ of tumor tissue. This provides a re-defined histological image having at least 400 million pixels, at 40× magnification (0.25 μm/pixel), or at least 200 million pixels, at 20× magnification (0.50 μm/pixel). The direct use of the raw or re-defined histological image when parameterizing the statistical function may thus involve high computational resources. By extracting one or more maps from the histological image and then discarding the histological image, all before the parameterizing, any method herein may perform an efficient parameterizing thus reaching high accuracy of the statistical function. In particular, each map may comprise less than 1 million or even 500 thousand pixels.

The attribute distributions may comprise any one or any combination of a distribution of tissue textures (i.e., a representation of spatial distribution of tissue types in the slide), a distribution of lymphocyte presence (i.e., a localization of lymphocytes in the slide), and/or a distribution of cell density (i.e., a representation of spatial distribution of cell count in the tumor slide), for example all three distribution types. Each map may cover the whole tumor slide (i.e., represent value of the attribute for all locations of the tumor slide, meaning that no part of the at least one histological image representing tissue is discarded, or no portion of the tissue thereof is preselected). For example, for each extracted map, every pixel of the map corresponds to a respective portion of the at least one histological image such that the map covers the entirety of the initial tumor slide image or of a part therein representing the entirety of the tumor tissue. Such map extraction reduces the information contained in the at least one histological image to the information relevant for prognosis, while maintaining spatial link in the information. The visual data may comprise or consist of the one or more maps (e.g., in whole). Alternatively or additionally, any method herein may comprise processing the one or more maps (e.g., in whole, that is, everywhere) to extract another type of visual data (such as features).

The one or more maps may comprise several maps (i.e., at least two) each representing a respective attribute distribution, for example a map representing a distribution of tissue textures, another distinct map representing a distribution of lymphocyte presence, and yet another distinct map representing a distribution of cell density. This specializes maps and, according to tests, provides high efficiency.

At least one (e.g., each) map may be extracted from the at least one histological image via a respective convolutional neural network (CNN). CNNs allow exploiting spatial coherency of information in images, such that their use allows obtaining accurate maps. Any (e.g., each) such CNN may be pretrained before any method herein, or trained independently within any method herein (i.e., separately from the training of the potential other CNN(s) and/or separately from—e.g., prior to—the step of parameterizing the statistical function). Such separate trainings allow convergence of the optimizations involved in the trainings (e.g., stochastic descent), thus allowing to reach workable CNN(s), that is, able to extract useful information from the histological image (which is a very heavy image to process otherwise). This further allows to process the whole image or all at least all the tumor tissue representation therein in spite of its large initial size, rather than select arbitrary portions of interest therein and thereby potentially discard useful information in non-selected portions.

In particular, the one or more maps may comprise a texture map extracted from the at least one histological image via a first CNN, and/or a lymphocyte map extracted from the at least one histological image via a second (distinct) CNN. The texture (respectively, lymphocyte) map may have pixels, and each pixel represents a texture (respectively, indicates lymphocyte presence) as a result of classifying a respective tile (i.e., patch) of the at least one histological image with the first (respectively, second) CNN. In other words, the first (respectively, second) CNN is an image classifying CNN applied to tiles of the at least one histological image. By "image classifying CNN", it is meant a CNN which takes as input an image and outputs a class of the whole image (e.g., a label among a predetermined plurality of labels each representing a respective one of a set of classes). Thus, the extraction of such map(s) from the at least one histological image may comprise subdividing the at least one histological image in tiles, processing each tile independently by the first/second CNN (sequentially or in parallel), and reconstructing the map from the outputs of the CNN applications. Each tile yields one pixel in the corresponding map. The subdivision in tiles may be the same or different for the texture map and the lymphocyte map, such that these two maps may have different resolutions. The use of classifying CNNs allows obtaining efficiently accurate maps. Image classifying CNNs indeed perform efficiently on whole images, such that the proposed approach achieves high efficiency relative to localizing several objects such as cells within single images and processing the cells one-by-one.

Additionally or alternatively, the one or more maps may comprise a density map extracted from the at least one histological image via a third CNN (distinct) CNN. The cell density map may have pixels each representing a local number of cells (i.e., number of cells at the location represented by the pixel), and each pixel results from counting a number of cells in a respective tile of the at least one histological image with the third CNN. The third CNN may thus be an image-processing CNN, and more particularly an object detection/localization CNN. This also provides high efficiency to determine cell density, as object-counting CNNs perform efficiently on whole images.

The statistical function may comprise a regression model, for example a Cox (e.g., survival) model, a stochastic model, or yet a neural network taking the one or more maps as input, and also taking the genomic data (e.g., cell-type distribution, for example in the form a score vector computed based on gene expression data as above, such as based on a log2 function and/or a geometric mean) and clinical data (e.g., in the form of a vector of numbers) also as further input, and outputting one or more predictions based on such input.

In the case of a neural network, the neural network may for example comprise one or more convolutional layers to process the one or more maps and provide one or more intermediate outputs, then one or more pooling layers to process each intermediate output and provide a respective vector per intermediate output, and then one or more fully connected layers (also referred to as "dense" layers), taking at least the respective vector(s) provided by the one or more pooling layers, so as to output the one or more predictions. The genomic data and the clinical data may be numeric and entered at any stage in the network, for example inputted to the one or more fully connected layers. For example, the genomic data and the clinical data may each be in the form of a respective numeric vector, and concatenated with the respective vector(s) provided by the one or more pooling layers into a single global vector (also referred to as "feature") which is then inputted to the one or more fully connected layers. The neural network is said to be a "multimodal" model in such a case. Alternatively, the genomic data and the clinical data may each be in the form of a numeric vector, and each separately inputted to one or more respective fully connected layer to provide a respective modal prediction, the respective vector(s) from the visual data (i.e., provided by the one or more pooling layers) being themselves separately inputted (e.g., optionally after being concatenated together) to one or more respective fully connected layer to provide yet a respective modal prediction. And all modal predictions may then be weighted by one or more final fully connected layers. The neural network is said to be an "ensemble" model in such a case.

The proposed solution may provide useful and personalized information for a patient from medical image data, genomic data, and clinical data. The predicted outcome (i.e., output of the statistical function) may comprise, for instance, cancer growth dynamics without treatment (e.g., evaluated as the time for tumor doubling or the time of relapse), treatment efficacy or any other biological tumor characteristic. The solution provides macroscopic information (e.g., on tumor evolution and on patient outcome) from only microscopic data (histological images), completed by genomic and clinical data.

In the prior art, images are sometimes analyzed to quantify the number of cells or quantify specific tissue characteristics. These extracted values are then used as risk scores, considering said values as directly associated with the predicted outcome. In general, this class of methods are based on thresholds. The accuracy and generalization of the prediction are limited by the threshold definition.

Unlike such prior art, the proposed solution may exploit all this information in a combined model containing the images, the genomic data, and the clinical data, and using it to produce a phenotypic prediction. This is neither a complete descriptive analysis of the data, nor a prediction based on small pieces of information. This may rather be a prediction based on a complete set of patient data, not directly dependent on a threshold.

Implementations of the proposed solution are now discussed.

From histological images of a patient, different CNNs may be applied to get a cell density map, a lymphocyte map and a texture map (that classifies the tissue type). From these three results, enriched by genomic data (coming from RNA or DNA sequencing) and clinical data, a statistical function may provide predictions for patient cancer outcomes. Few assumptions may be required to achieve such result, and the solution may involve a complete use of whole slide images, making the proposed approach particularly accurate and individualized.

Generally, a therapeutic decision lies on an average of a considered biomarker concentration (for instance, number of lymphocytes Vs number of cancer cells). However, this quantity is known to be spatially heterogeneous and the same average number could lead to very different outcomes depending on the spatial distribution of the biomarker (Saltz et.al and Corredor et. al.). Eidel et. al. have shown that patient prognostic can be predicted only if spatial heterogeneity of lymphocytes are considered, in the case of breast cancer. To overcome this limit, recent prior art considers different regions of interest: the center of the tumor and the invasive front or tumor boundary (Pages et. al). Moreover, the average concentration of a biomarker (on a single area, or on two sub-regions) is generally compared to a threshold (often fixed heuristically).

Unlike such prior art, in implementations of the proposed solution, no area is predefined, and the whole slide image of tumor tissue is completely used. The spatial heterogeneity of the biomarker reflects biological activity of the cells. Thus, by using the whole slide image, more information on disease is caught by the proposed model, thereby leading to better predictions. In addition, the proposed solution may perform without any threshold, such that less a priori information is used.

Figure 2:
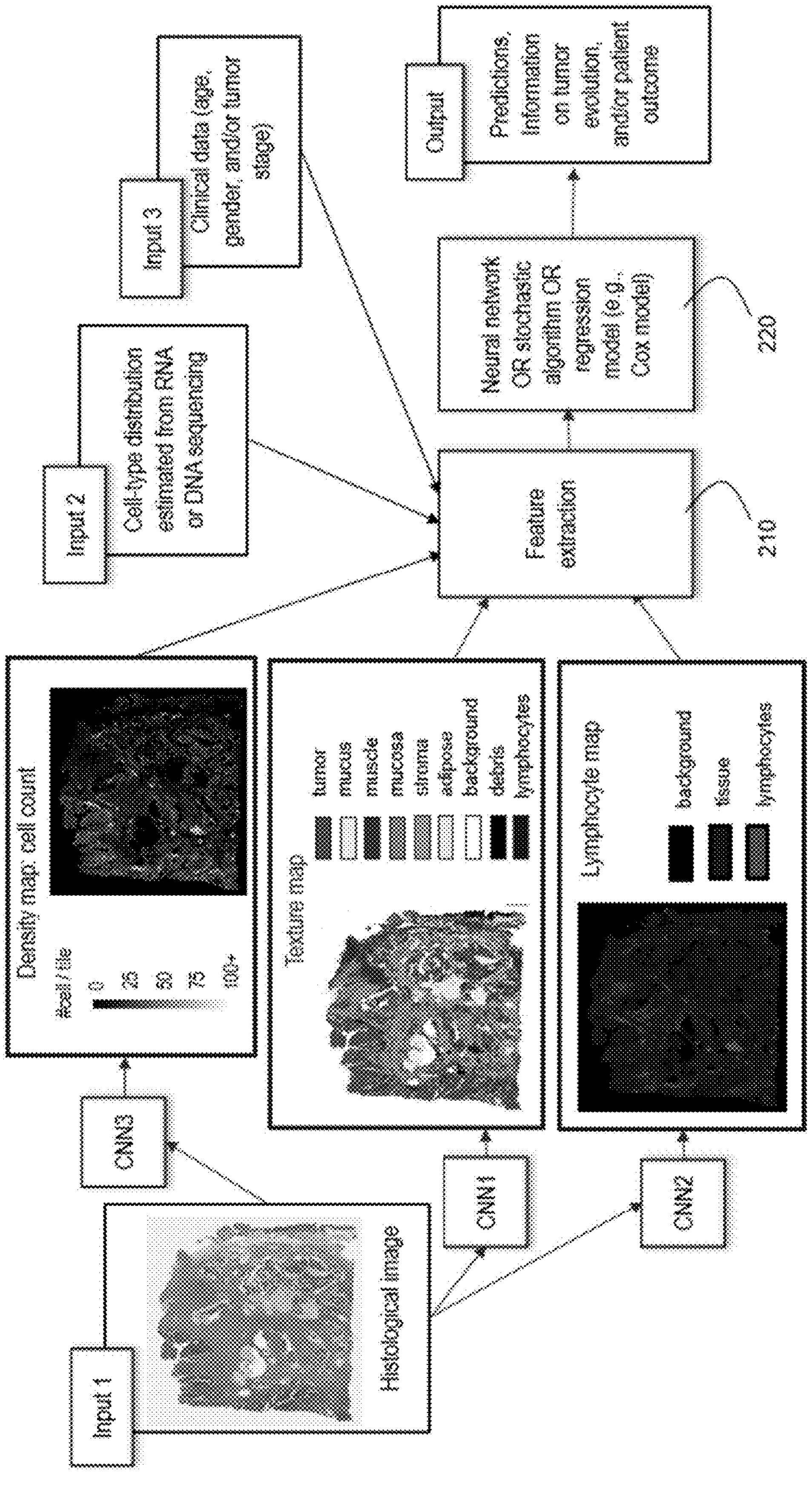
FIGS. 2, 3, and 4 illustrate the proposed solution.

FIG. 2 shows an example of the statistical function and its inputs and outputs.

On the figure, Input 1 is shown to be a histological image of tumor slide, such that the dataset may include histological images of this kind for a plurality of patients. Thus, the statistical function comprises CNN1, CNN2, CNN3, a feature extraction block 210, and a further block 220 which consists of a neural network or a regression model (such as a Cox model). Alternatively, rather than the histological images, the dataset may be populated with the maps resulting from the CNNs, or yet with the features extracted in block 210. In such a case, the statistical function comprises only block 210 and block 220, or yet only block 220. In the former case, the maps resulting from the CNNs are inputs of the statistical function rather than the histological images, and the CNNs constitute a pre-processing in the dataset-forming method and in the use method. In the latter case, the features resulting from block 210 are inputs of the statistical function rather than the histological images or the maps, and both the CNNs and block 210 constitute a pre-processing in the dataset-forming method and in the use method. This is all a matter of implementational details.

In addition, this example is discussed with respect to patients affected by a colorectal cancer disease. But this is merely for illustrative purposes, and the example may apply to other cancer diseases provided that the training datasets and the tissue/texture classes are accordingly adapted.

Input 1 consists of at least one histological image coming from a tumor biopsy or surgical resection, cut in thin slides and observed at a high microscopic magnification to produce, high resolution image. The at least one histological image may represent only a size of tumor tissue of the order of the square centimeter millimeter or even the square millimeter, and yet it may contain contains billions of pixels.

Input 1 may thus be a very large image (high resolution, billions of pixels). The image may be subdivided in tiles or patches (order of magnitude: each tile may be of size 224×224 pixels or 448×448 pixels, depending on the image magnification, and one image may contain from 10 000 tiles to around 200 000 tiles).

For each image tile, three different CNNs may be applied, in order to produce three different maps, that is, a texture map, a lymphocyte map, and a density map:

CNN1: Similar to the CNN disclosed in Kather et. al., and trained on the dataset disclosed therein, a first CNN may classify the tile depending on its texture, i.e., its biological nature (e.g., in nine classes in the case of a colorectal cancer, including tumor, stroma, muscle, background, adipose, debris, lymphocyte, mucus, normal mucosa More generally, and whichever the type of the cancer disease, the first CNN may classify the tile according to a predetermined set of classes including any combination of the following classes: tumor, stroma, muscle, background, adipose, debris, lymphocyte, mucus, and/or normal mucosa. The spatial juxtaposition of the results from all the tiles to reconstruct the original image yields a texture map (called also a tissue map). This first CNN may be pre-trained on the ImageNet database (not specific to medical images, but also used to recognize cats and dogs for example). This speeds up the training as this reduces over-fitting. CNN1 may further be trained on a colorectal database (accessible at the following URL at the priority date of the present application: zenodo.org/record/1214456#.XmirLpNKiqA) of annotated tiles, where an annotation may provide the class of the patch/tile: tumor, background, lymphocytes, stroma, mucosa, mucus, muscle, adipose or debris.

CNN2: Similar to the CNN disclosed in Saltz et. al., and trained on the dataset disclosed therein, a second CNN may classify each tile depending on the presence of lymphocytes (e.g., according to a threshold of confidence, wherein the threshold may be automatically computed as the optimal value that leads to optimal results relative to the database used for the training). The spatial juxtaposition of the results from all the tiles yields the lymphocyte map. The lymphocyte map provides comprehensive information on immune response, as the texture map may classify tiles as "tumor" rather than "lymphocyte", even when lymphocytes are present in the tile. This second CNN may also be pre-trained on the ImageNet database, and may be further trained on another database (accessible at the following URL at the priority date of the present application: stonybrookmedicine.app.box.com/v/cellreportspaper) of annotated tiles from various cancers, each annotation classifying the patch in category with or without lymphocytes.

CNN3: A third CNN, a Mask R-CNN, similar to the CNN disclosed in He et. al., may count the number of cells in each tile. The spatial juxtaposition of the results from each tile yields the density map of cells in each tile. This third CNN may be pre-trained on a nuclei database from the 2018 data science bowl (accessible at the following URL at the priority date of the present application: www.kaggle.com/c/data-science-bowl-2018), in which cell nuclei are segmented on various kinds of medical images, and may further be trained on another database (accessible at the following URL at the priority date of the present application: monuseg-.grand-challenge.org/) in which cells nuclei are segmented specifically on hematoxylin and eosin (H&E) images.

In each of these three CNNs, the spatial juxtaposition step is a 2D juxtaposition of the tiles, inverse to how the tiles are initially built from the initial image (by the subdivision of the initial image). More concretely, if an input histological image is cut in 200×150 tiles (i.e., grid of tiles), the output aggregated result may be an image that contains 200×150 pixels (each tile becomes a single pixel in the aggregated output image).

The example thus implements a combination of the output of these three CNNs, further combined with non-visual features (input 2 and input 3, linked to patient DNA or RNA and clinical data).

In variations, only one of these three CNNs or any combination of two of these three CNNs may be implemented, rather than the three of them.

Cell detection and classification have been already combined (see Jackson, H. W. et. al. (2020) and Yuan, Y., (2012)) in a different way. Jackson et al (2020) used the PhenoGraph library to clusterize cells and identify cellular "metaclusters" or communities based on the cells phenotypical similarities. They then used marker expressions and cell-shape features to classify each metacluster into a cellular subgroup. Yuan (2012) on the other hand used an SVM classifier to attribute a class to each cell based on morphological features and then analyzed the overall architecture of cell classes. These solutions, as most other similar ones, suggest identifying and classifying each cell in a single pass, which yields only microscale information on individual cells (Yuan, 2012) or clusters of cells (Jackson & al., 2020).

The example solution rather treats each scale separately, with distinct CNNs. Cellular information (microscale) is rendered through a density map, and tissue information (mesoscale) is rendered through texture and lymphocyte maps. Thus, instead of individually classifying each cell as a tumor/stromal/lymphocyte cell, the example solution classifies whole tiles (patches) so as to keep information on spatial organization, while still get quantitative information on cells densities. This has several advantages:

This is less costly than individual-cell analysis, thus allowing to analyze whole slide images of great sizes.

This allows to classify more types of tissue that do not necessarily contain cells, like mucus or adipose.

Patch classification is analogous to image classification, since each patch is treated as an image by the CNN, yet image classification yields better results in general than cell classification (95+% accuracy Vs 90+% accuracy).

Cell detection is computationally expensive. By discarding such input, the solution achieves high efficiency.

Thus, given the lymphocyte and texture maps, the example solution extracts useful information on tumor evolution, e.g., without or under treatment. The input is enriched with a density map (also part of input 1), with cell-type distribution (input 2), and with clinical data (input 3) in order to improve the quality and the accuracy of the result. The input cell-type distribution may be estimated from RNA or DNA sequencing by any method (e.g., deconvolution method or any other). For each patient, the solution may thus extract the gene expressions corresponding to some cell populations. The input of the cell populations' distribution is complementary data to the density, textures and lymphocytes map. The combination of genomic and visual information is useful because the maps outputted by the CNNs contain spatial information while the cell-types distributions do not (since these distributions may be global distributions on the entire tumor). Also, the cell-type distribution contains more information on cell categories: immune cell types may be subcategorized in T cells helper, T cells cytotoxic, T cells regulatory, B cells; tissues may be subcategorized in fibroblast, myeloid cells, neuronal cells. Cell subcategories information is not present in the maps, such that adding genomic data complements the visual material.

The statistical function may take different forms: neural network, regression model, stochastic or statistic algorithm, and/or combination of those. If the statistical function comprises or consists of a supervised machine learning method, the statistical function may be trained on a complete dataset (histological images, RNA or DNA sequencing, clinical data) with patient-specific clinical endpoint/outcome annotations (for instance time of relapse or time of death). If the statistical function comprises or consists of a non-supervised machine learning algorithm, the solution may perform a clustering in order to assign patients to a category with other similar patients, and therefore, link their survival to the survival of patients in the same cluster. The statistical function may also comprise a regression model (i.e., a Cox model), a machine-learning models (e.g., random forest classifier or neural network) to predict the patient outcome at different time steps based on these features. For example, given a set of visual features like number of tumor cells and number of lymphocytes near the tumor, the statistical function may predict the survival probability of a patient at six or twelve months.

According to the form of the model, a first step of extraction of specific spatial features from the output maps may be performed by block 210. Features may include: number of tiles (patches) and cells for each texture, number of lymphocytes near the tumor, and/or spatial organization of these lymphocytes (e.g., including clustered and/or scattered). Those visual variables may be inputted into block 220, for example a survival prediction model such as the Cox model to quantify the influence of each of these features on the patient outcome.

Figure 3:
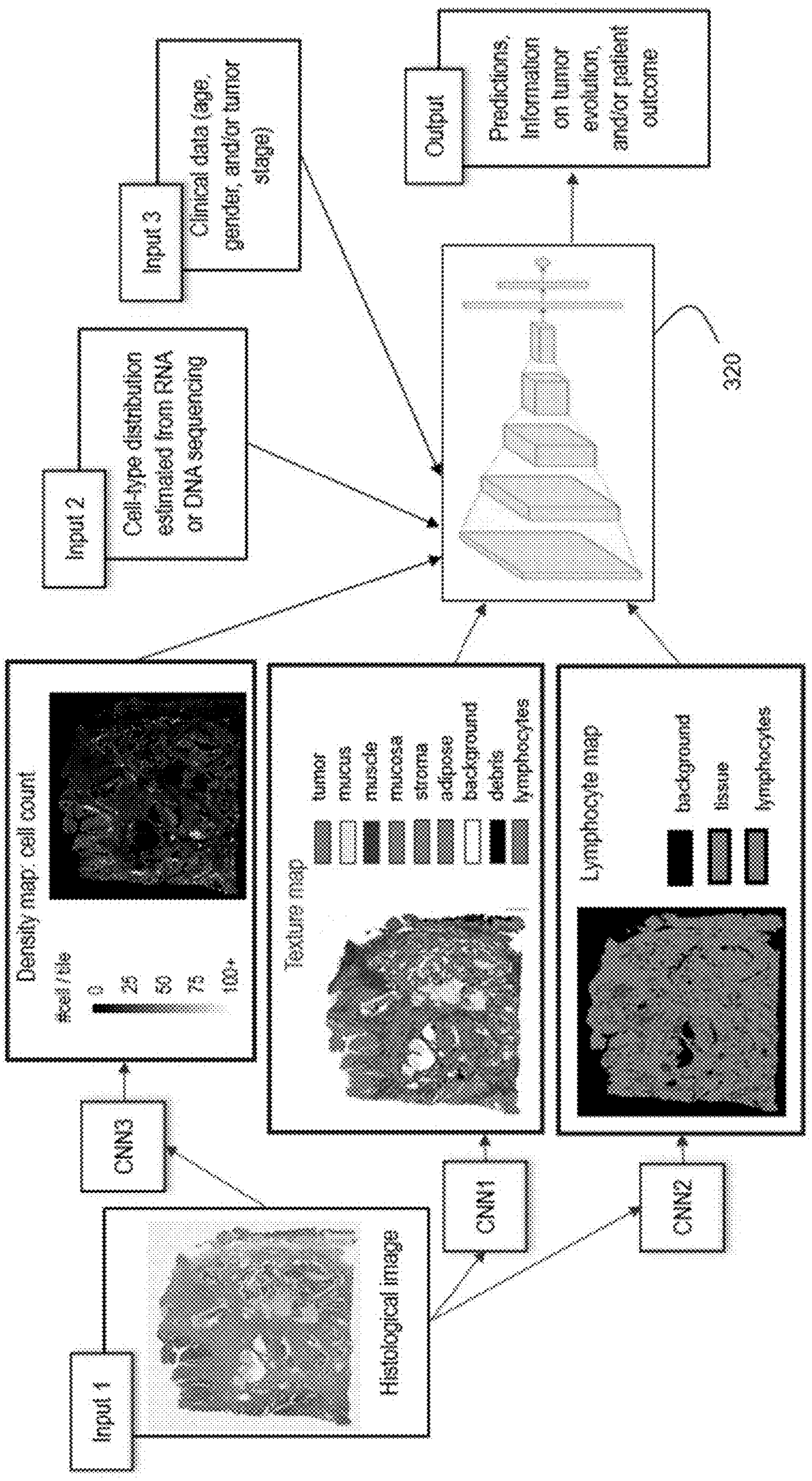

FIG. 3 shows a variation of the example of FIG. 2. In this variation, the statistical function comprises no feature extraction block and the maps resulting from the CNNs are directly input in a neural network 320. The neural network 320 may for example comprise convolutional layers to process the maps, and fully connected layers to perform classification. The genomic data (input 2) and the clinical data (input 3) may be numeric and entered at any stage in network 320 (e.g., at one of the fully connected layers). For example, the convolution layers may be followed by one or more pooling layers and reduce the maps into a feature vector, and input 2 and input 3 may be numeric vectors concatenated to such a feature vector. Fully connected layers may then process the feature vector.

Figure 4:
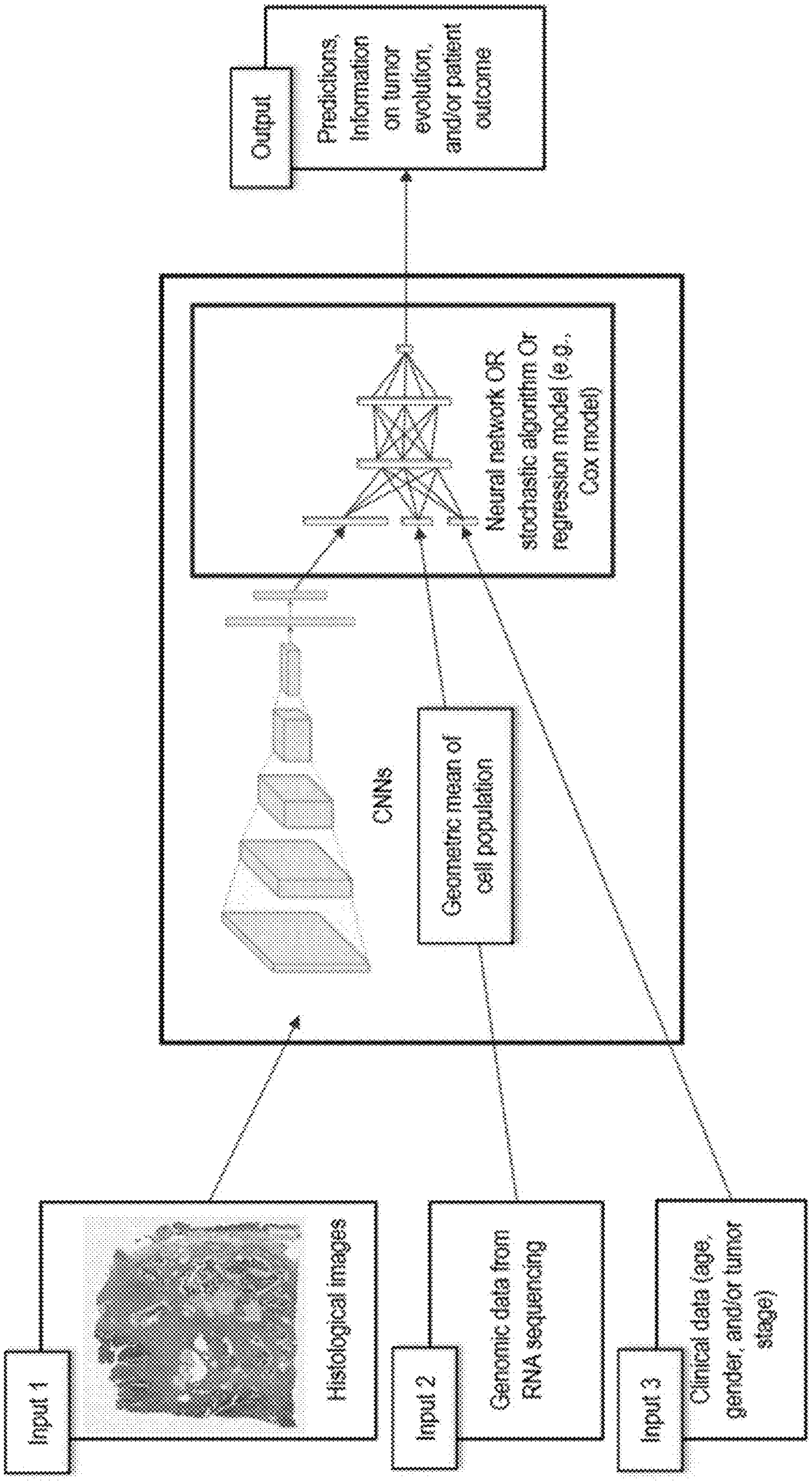

FIG. 4 shows a variation of the example of FIG. 3. In this variation, the at least one histological image (input 1) is directly passed into CNNs part of the statistical function (i.e., no map extraction is performed). In addition, the genomic data may optionally be processed by extracting a geometric mean of the data therein or passed through a neural network, to output a vector which may be concatenated to a result of the CNNs processing input 1.

A complete pipeline that was tested and in line with the example of FIG. 2 is now discussed with reference to FIGS. 5-15.

1. Data Retrieval

The first step was to gather data. To do so, a study on colorectal cancer from The Cancer Genome Atlas (TCGA) on the website cbioportal.org was selected. The study contained the IDs of 640 patients, with their clinical information and survival time and status. From the IDs of these patients, the histological slides and genomic data of 616 of them could be retrieved from the TCGA Genomic Data Portal. To do so, the gdc-client tool was used to request the image and genomic files IDs for each patient, and a manifest was built and used to download all the required files from the portal.

At this point, clinical, genomic and visual data were available for each patient:

- The clinical data consisted of a (e.g., excel) worksheet with the following information: patient ID, age, gender, tumor stage (1 to 4), lymph node stage (0 to 2), metastasis stage (0 or 1), cancer type (mucinous or not), primary tumor site (cecum, ascending colon, hepatic flexure, transverse colon, splenic flexure, descending colon, sigmoid, recto-sigmoid or rectum), lymphovascular invasion (yes or no), vascular invasion (yes or no), MSI/MSS sensor score, neo-adjuvant therapy administered prior to tumor resection (yes or no), overall survival in months, overall survival status (living or deceased).
- The genomic data consisted of a (e.g., .txt) text file for each patient containing the gene expression values of 60483 genes. The genes may be identified with their ENSEMBL code (for example: ENSG00000089692 for the Lymphocytes Activating Gene 3). The gene expression value may be calculated as the Fragments Per Kilobase of transcript per Million mapped reads (FPKM), obtained from RNA sequencing.
- The visual data was a (e.g., .svs) diagnostic slide image for each patient, with size ranging from thousands of pixels to billions.

The next step was to process these three types of data to obtain useful variables.

2. Visual Data Processing

To process the .svs slides, three CNNs were trained as explained in reference to FIG. 2: one adapted to recognize nine classes (tumor, stroma, muscle, background, adipose, debris, lymphocyte, mucus, and normal mucosa), one adapted to specifically recognize lymphocytes, and one adapted to locate individual cells.

These three CNNs were applied to each of the patients' slide following the steps detailed below.

Figure 5:
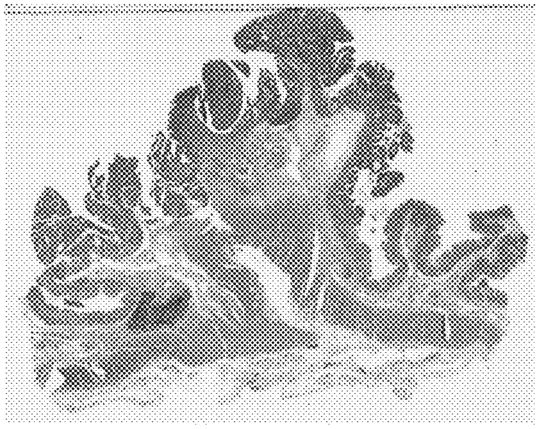
FIGS. 5, 6, 7, 8, 9, 10, 11, 12, 13, 14, 15, 16, 17, 18 and 19 illustrate tests that have been performed.

FIG. 5 shows one patient's slide (Patient ID: TCGA-3L-AA1B (95615×74462 pixels) to illustrate the process.

First, the .svs file is loaded with the OpenSlide library and the image thumbnail (a smaller version of the slide) is opened. It is converted to grayscale and the OTSU threshold method is applied to find the main tissue area.

Figure 6:

FIG. 6 shows the result.

The location of the tissue patches is then interpolated from this smaller image, to the slide at its maximum magnification level. Thus, a pixel identified as tissue on the thumbnail is marked as a tissue patch on the whole slide image. This pre-segmentation step allows to filter out most of the background and saves a lot of computation time.

Once the coordinates of the tissue patches are obtained, the pipeline may run over the whole slide image patch by patch. The patches may be of size 224×224 if the slide magnification is 0.25 microns per pixel (mpp), and 448×448 if the magnification is 0.23 mpp. This choice is due to the fact that the machine used during slide digitization causes big differences in resolution sizes: 0.23 mpp is almost twice as big a resolution as 0.25 mpp. The 448×448 patches are then reduced to the size of 224×224 to fit into the CNNs. Smaller patches could alternatively be used.

Each tissue patch is sharpened/unblurred if needed (e.g., by using the Pillow library ImageFilter module which contains an "ImageFilter.SHARPEN" parameter in Python). This sharpening step yields better classification results: some patches can be blurry (due to the digitalization steps in the creation of the .sys image) and the blur induces error in classification. This is a common pre-processing step in image processing. The patch is then normalized depending on its contrast. Two different kinds of normalization are applied depending on the contrast value: Macenko or Reinhard. The contrast value depends on the hematoxylin & eosin staining process and on the slide digitization machine. Thus, the contrast threshold to select one normalization or the other was found empirically. There are different methods for stain normalization besides Macenko and Reinhard (i.e., Histogram Specification, Vahadane normalization, etc.), but those two were selected because: Macenko is the gold-standard of normalization when the contrast is low, and Reinhard is the faster default when stain contrast is already high. Other normalization methods may be implemented. The normalization step allows better classification results.

The patch is given as input to the cell detection CNN, and it outputs the coordinates of each cell it has located inside the patch.

Then the normalized patch is given to the texture CNN: two texture CNNs were trained, one on Macenko normalized data, and the other on un-normalized data. The pipeline uses one or the other depending on the whole slide image resolution (0.25 mpp or 0.23 mpp) and the patch normalization (Macenko or Reinhard). The textures CNN outputs a value corresponding to the category of the patch: 0:"Adipose", 1:"Background", 2:"Debris", 3:"Lymphocytes", 4:"Mucus", 5:"Muscle", 6: "Normal mucosa", 7: "Stroma", 8: "Tumor".

For the lymphocytes CNN, the input patch may be of size 100×100 pixels. Thus, the 224×224 normalized patches are either cut into 4 sub-patches or resized, depending on the image magnification, and fed into the CNN. It outputs 1 if the sub-patch contains lymphocytes, and 0 if it does not.

As each patch is processed, a map is constructed for each task:

- a density map where each pixel value is the number of cells found within the patch,
- a texture map where the pixel value is the number of the category of the patch, and
- a lymphocyte map where each pixel value is zero or one depending on whether the sub-patch has lymphocytes or not.

A json file may also be constructed which stores the individual locations of all the cells found by the detection CNN for later visualization and record-keeping.

Once all the tissue patches have been processed, the three reconstructed maps can be visualized.

Figure 7:
Figure 8:
Figure 9:

FIGS. 7-9 respectively show the texture map, the lymphocyte map, and the density map.

This process was applied on all 616 patients' slides. A manual verification of the output maps may be performed to eliminate slides on which the process is not successful. For example, this may include slides with big pen marks made by the pathologists, slides of bad quality (i.e., too little tissue or bad staining making it impossible to distinguish tissues) and slides without any tumor. This process was done manually, but it could potentially be automated as a sorting test before processing the image. Once these images were removed, the pipeline reached the number of 558 patients.

From these maps, the pipeline comprises extracting numerical features that can be used as variables for the prediction model. The pipeline extracts for each patient:

The ratio of patches for each of the nine categories (their sum being 100%).

The ratio of cells in each of the nine categories (except for the background).

Figure 10:
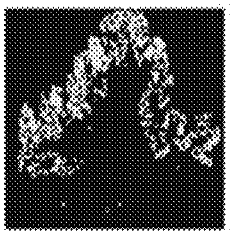
Figure 11:
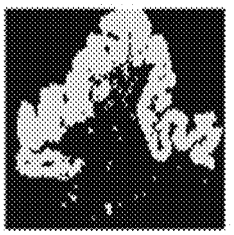
Figure 12:
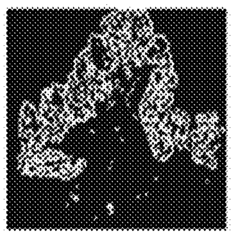
Figure 13:
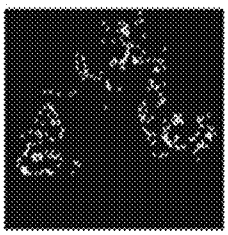

The ratio of lymphocytes patches near the tumor area. "Near the tumor area" means among the tumor patches and around them (although alternatively the process may go beyond the adjacent patches), as illustrated by FIGS. 10-13. To find the lymphocytes patches inside and around the tumor area, the pipeline first looks at only the tumor patches (FIG. 10). Then, the pipeline considers these patches as one object, and pipeline fills its holes to find the non-tumor patches among them. The pipeline also moves it by one pixel in each of the eight directions possible to encompass the area around our object FIG. 11). As mentioned above, the pipeline could alternatively increase the number of pixels considered for the near region area. The pipeline then subtracts the image of FIG. 10 to the image of FIG. 11, and this yields the non-tumor patches inside and around the tumor area (FIG. 12). The pipeline can then look at the amount of lymphocytes patches that are among these (FIG. 13) and divide this by the amount of total tissue patches to have the ratio of lymphocytes patches near the tumor area.

The ratio of lymphocyte cells near the tumor area, with the same process as above but with cells.

The ratio of stroma patches near the tumor area, with the same process as above but with stroma patches.

The tumor neighbors: this is the mean number of neighbors from each class for each tumor patch. Thus, the pipeline looks around at the eight neighbors of each tumor patch and counts how many times these neighbors are of each texture (adipose, mucus, stroma, etc.).

The Ripley's K index for stroma and lymphocytes, taken at five different radii: this is a measure of how clustered our data is. The pipeline defines a radius around each of our chosen texture patches, and a score is outputted depending on how many patches of this particular texture were found in this radius. The more clustered the data is, the higher the score.

Figure 14:
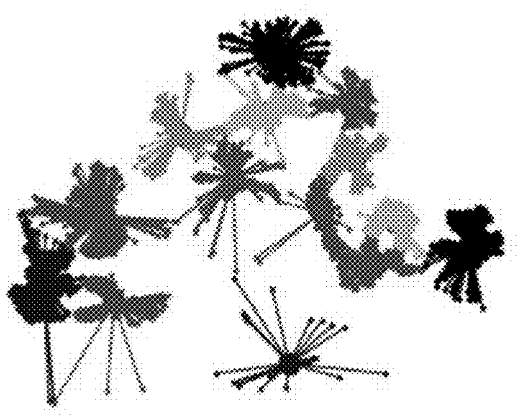

The affinity propagation measures for the lymphocytes: this is also a measure of how clustered the data is. This particular algorithm finds the number of clusters of lymphocytes, and the pipeline can extract measures for each patient such as the number of clusters, the mean number of patches in each cluster, the mean dispersion of the clusters, the mean maximum distance of patches within the clusters, the determinant ratio index which indicates how connected our clusters are, and a c index which indicated how compact our clusters are. FIG. 14 shows the result of the affinity propagation of clusters of tumor-infiltrating lymphocytes.

After a study of the Pearson correlations between these features, it was found that some of them were highly correlated, as expected. The pipeline therefore settled on the following fourteen features that have low correlations or that carry complementary information:

the ratio of adipose patches,
the ratio of debris patches,
the ratio of mucus patches,
the ratio of muscle patches,
the ratio of normal mucosa patches,
the ratio of stroma patches,
the ratio of tumor cells,
the ratio of lymphocytes cells,
the ratio of stroma patches near the tumor,
the ratio of lymphocytes cells near the tumor patches,
Ripley's K index for stroma with a 5 pixel radius,
Ripley's K index for lymphocytes with a 5 pixel radius,
the affinity propagation determinant ratio index, and
the affinity propagation c index.

For patient TCGA-3L-AA1B for example, the tumor cells ratio was 42.9998, the lymphocytes cells ratio was 22.2988, and the affinity propagation c index was 0.0165.

3. Genomic Data Processing

To process the genomic text files, the pipeline performed similarly to the paper Becht, E & al., 2016.

This paper comes with a worksheet that associates gene IDs with cell populations: for example the genes "207979_s_at" and "215332_s_at" are associated with CD8 T cells. They advise the reader to combine these genes to form a score for each cell population. The score is calculated as the log2 of the geometric mean of these genes' values.

The pipeline reproduced this method for the patients. However, in the present patients' files, genes are identified by their "ENSEMBL" codes whereas in the article mentioned above, genes are identified by their "probeset" code. Those are two ways of identifying genes. The pipeline therefore had to first find the correspondence between the probeset codes in the article (in the form "207979_s_at") and the ENSEMBL codes used in the patient's files (in the form "ENSG00000089692"). To do so, the biomart library was used, which allows to map these two kinds of IDs: if given a probeset code found in the article, biomart can yield the corresponding ENSEMBL codes, so that the values in the patients' files can be retrieved.

Then, for each patient, the pipeline calculated the score for each cell population given in the article: T cells, CD8 T cells, cytotoxic lymphocytes, B lineage, NK cells, monocytic lineage, myeloid dendritic cells, neutrophils, endothelial cells, and fibroblasts.

For patient TCGA-3L-AA1B for example, the score for CD8 T cells was 0.039163958, and the score for NK cells was −4.961284194.

4. Clinical Data Processing

The clinical data was also subject to some processing: the pipeline converted all the binary and cancer stage values to numbers (stage T2=2, yes=1, no=0, etc.). The primary tumor sites were converted to a binary value for "Left Tumor site" and "Right tumor site": if it is neither left nor right, then it is a rectal cancer. This is a classical way of locating the primary tumor site in the colon. The pipeline combined the lymphovascular and vascular invasions into a single variable called "VELI+": if the patient has either of these invasions then they are positive for this variable.

The pipeline converted the MSI/MSS sensor score into a binary value: 1 if the MSI sensor score is superior to 10, and 0 otherwise (the cutoff value of 10 was given in the study). The 11 patients that had neo-adjuvant therapy administered prior to the resection were discarded because mixing patients that have had treatment and patients who have not might bias the results. Finally, the 2 patients who had missing survival data we also discarded (because the predictions could not be verified for them), thus reaching the number of 623 patients.

5. Cox Lasso for Variable Selection

The pipeline used neighbors-based imputations on the clinical, genomic and visual missing data to have the largest set of patients with complete data possible: 623 patients. Without the imputations, this number dropped to 460 patients.

To know which variables among the clinical, genomic and visual variables, have an influence on patient's survival, the pipeline used a Cox model with a LASSO penalty. First, the pipeline includes all of our variables in the model and varies the penalty ($9\times10^{-10}$, $8\times10^{-10}$, $7\times10^{-10}$, $9\times10^{-9}$, $8\times10^{-9}$, . . . , 0.2, 0.1). For each penalty value, the pipeline only keeps the relevant variables: those that have a p_value<0.1. The pipeline separates the data into 5-fold (with twenty repetitions) and for each subset. A new Cox model is built using only the relevant variables. The pipeline calculates the concordance index score on the test subset. This is done a hundred times on the different subsets. The pipeline then looks at the mean concordance index score for each set of variables selected by the Cox model with LASSO, and takes note of the best score.

A Cox model is a survival model able to evaluate the effects of several variables on overall survival. For this, the Cox model calculates a coefficient to associate to each variable, the coefficient representing the influence that this variable has on survival. By combining the variables and their coefficients with a baseline risk of death, the Cox model can predict a risk score for each patient and a survival probability function. The Cox model with a LASSO penalty may be used to select the most relevant variables.

The model was evaluated with the concordant index, as this represents the ability of the model to rank patients by their time of death. It compares patients two-by-two and verifies whether the patient with the higher predicted risk score has indeed died before the other one.

In this case, the best concordance index of 0.7518 was given by the following set of variables on our imputed data: age, tumor stage, lymph node stage, metastasis stage, monocytic lineage, myeloid dendritic cells, fibroblasts, ratio of lymphocytes cells, ratio of lymphocytes cells near the tumor area, and affinity propagation c index.

From there, a Cox model was built using only this set of variables, and the pipeline predicted a risk score for each patient as well as their survival probability as different time steps.

Figure 15:
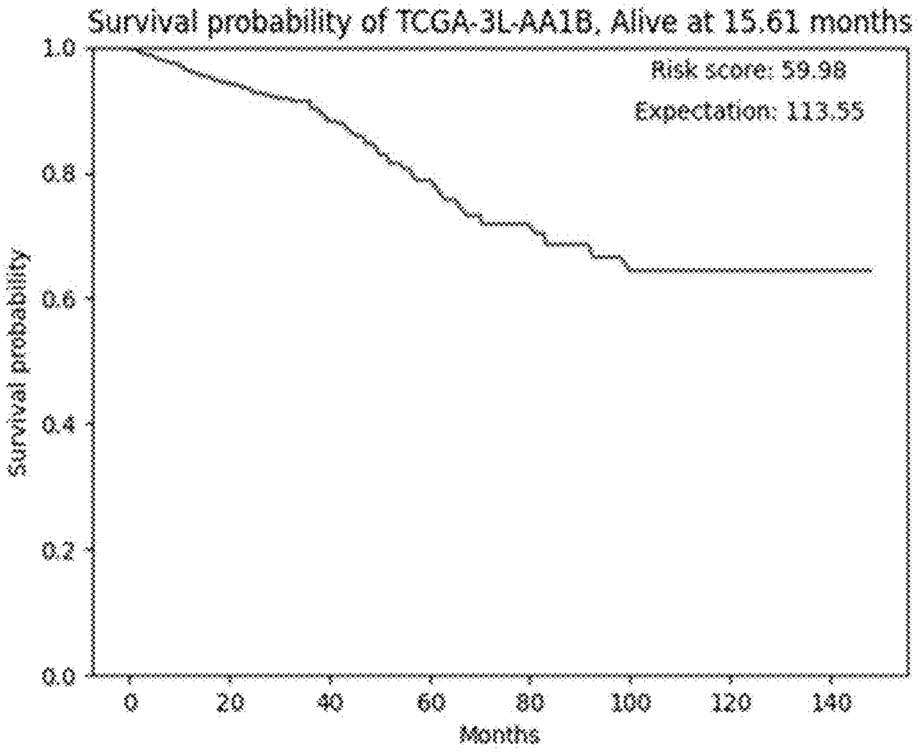

FIG. 15 shows an example of the survival probability for patient TCGA-3L-AA1B, as generated by the Cox model.

In variations of the above pipeline, the Cox model may be replaced with a deep learning model (neural network). The deep learning model may take as input the genomic data, the clinical data and the maps/masks (e.g., directly), thus removing the visual features selection step. Such a model may have the same output as the Cox model: a risk score for each patient. An advantage of deep learning models is that they may bypass the preselection of the set of fourteen chosen visual features for the prediction. Indeed, the model may learn by itself which visual features are relevant in the masks and combine them with genomic and clinical data to predict the risk score of a patient.

Such variations were tested on a dataset of 432 patients, as discussed in reference to FIGS. 16-19.

Figure 16:
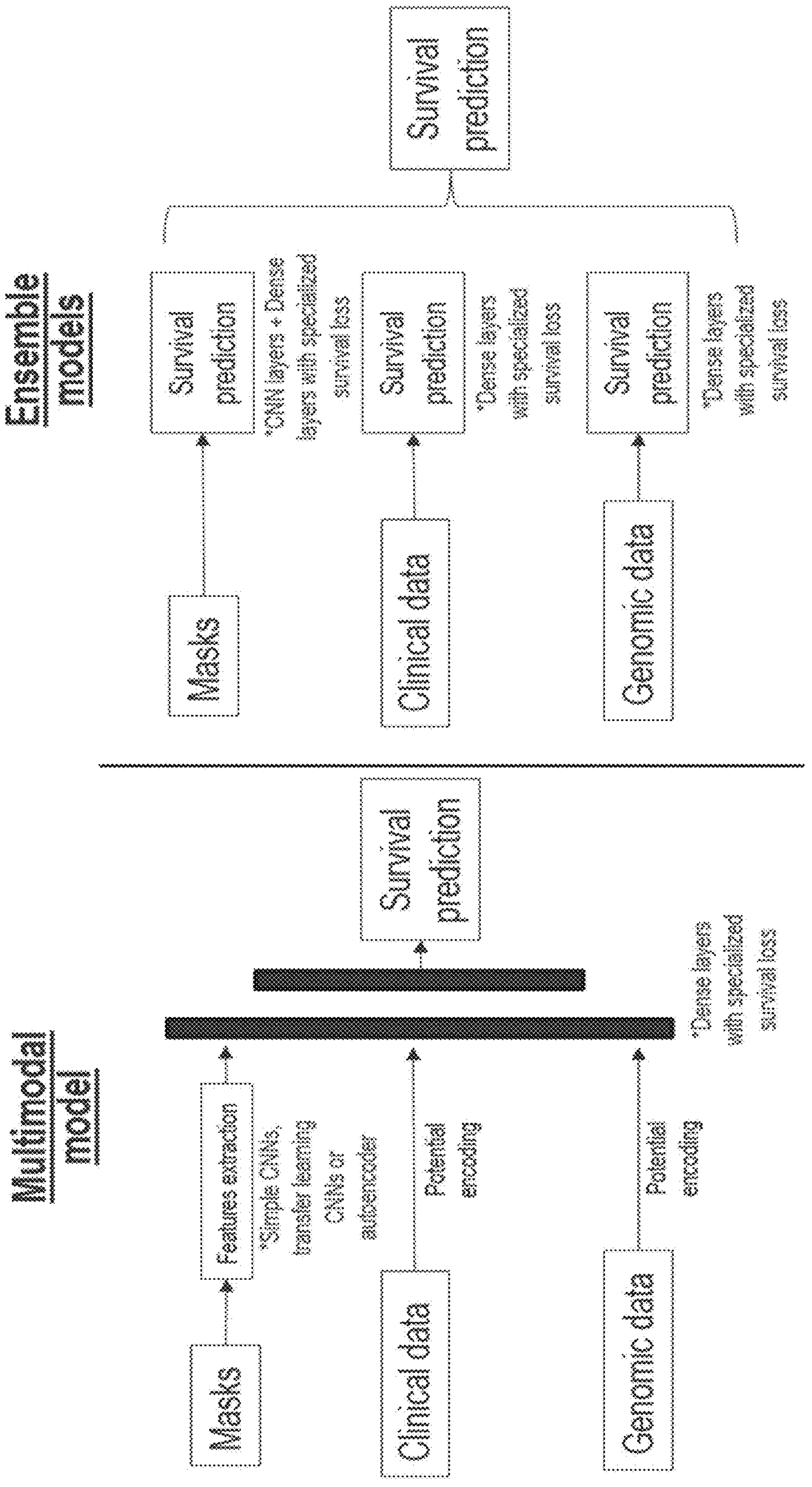

As shown by FIG. 16, at least two architectures may be implemented for deep learning survival models that take as input the masks, the clinical data and the genomic data: multimodal models and ensemble models.

Multimodal models directly combine the different inputs, and may provide a risk score based on the combination of these different data. The ensemble models may perform one risk score prediction for each kind of data: one prediction based on clinical data, one based on genomic data, and one based on visual data (the masks). The final output prediction may derive from a weighting of those three predictions. A dense layer may perform the weighting.

From this, several structures have been tested, namely:

A simple CNN was tested, which takes the three masks as inputs, applies several convolutional and pooling layers, and several dense layers. This output is then concatenated with the clinical and genomic data, and several dense layers are applied to make the final prediction. The maximum concordance index with this type of models was 0.6809.

The network that achieved this result had the following structure: for each mask of dimensions (762, 787, 1), four convolutional and pooling layers of kernel size (5,5) and pool size (2,2) are applied. The convolutional units are of the number 16, then 24, then 40, and then 48. A global average pooling is then applied to each of the outputs, providing three vectors of size 48 each. A dense layer is applied to each of them, which transforms them into three vectors of size 1000 each. These three vectors are then concatenated with the clinical data vector of size 10 and the genomic data vector of size 10, which provides a vector of size 3020. Then a dense layer is applied, outputting a vector of size 1512, and then the final dense layer which outputs a scalar (the risk score).

Figure 17:
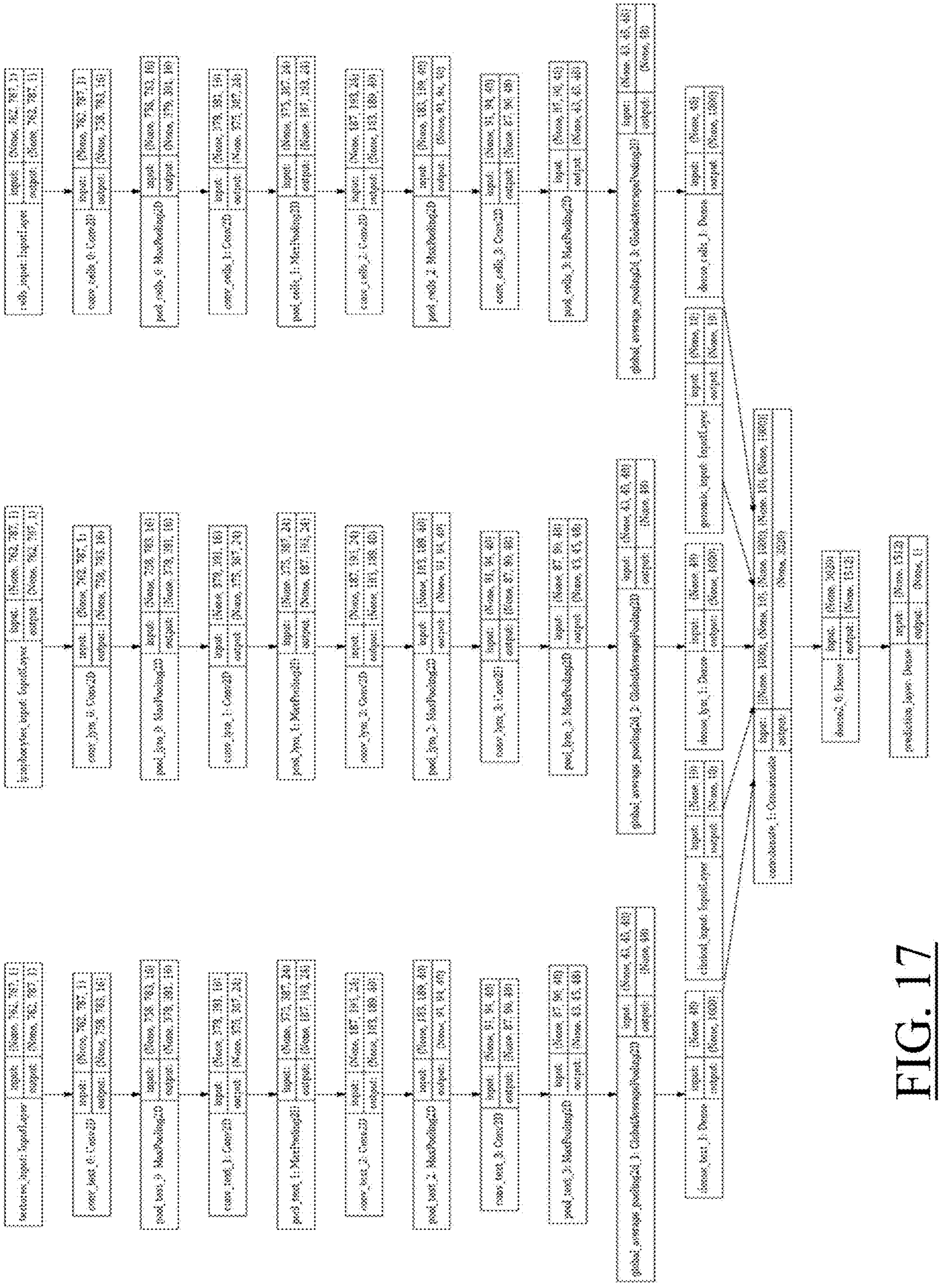

FIG. 17 shows the structure of this network.

Transfer learning models were also tested, in which the CNN taking the three masks as inputs is a pre-trained Keras model. The model selected for the tests was ResNet50, as it yields good results on classification databases like ImageNet (on which it was pre-trained), and as it is a relatively light model. The maximum concordance index with this type of models was 0.6792.

Figure 18:
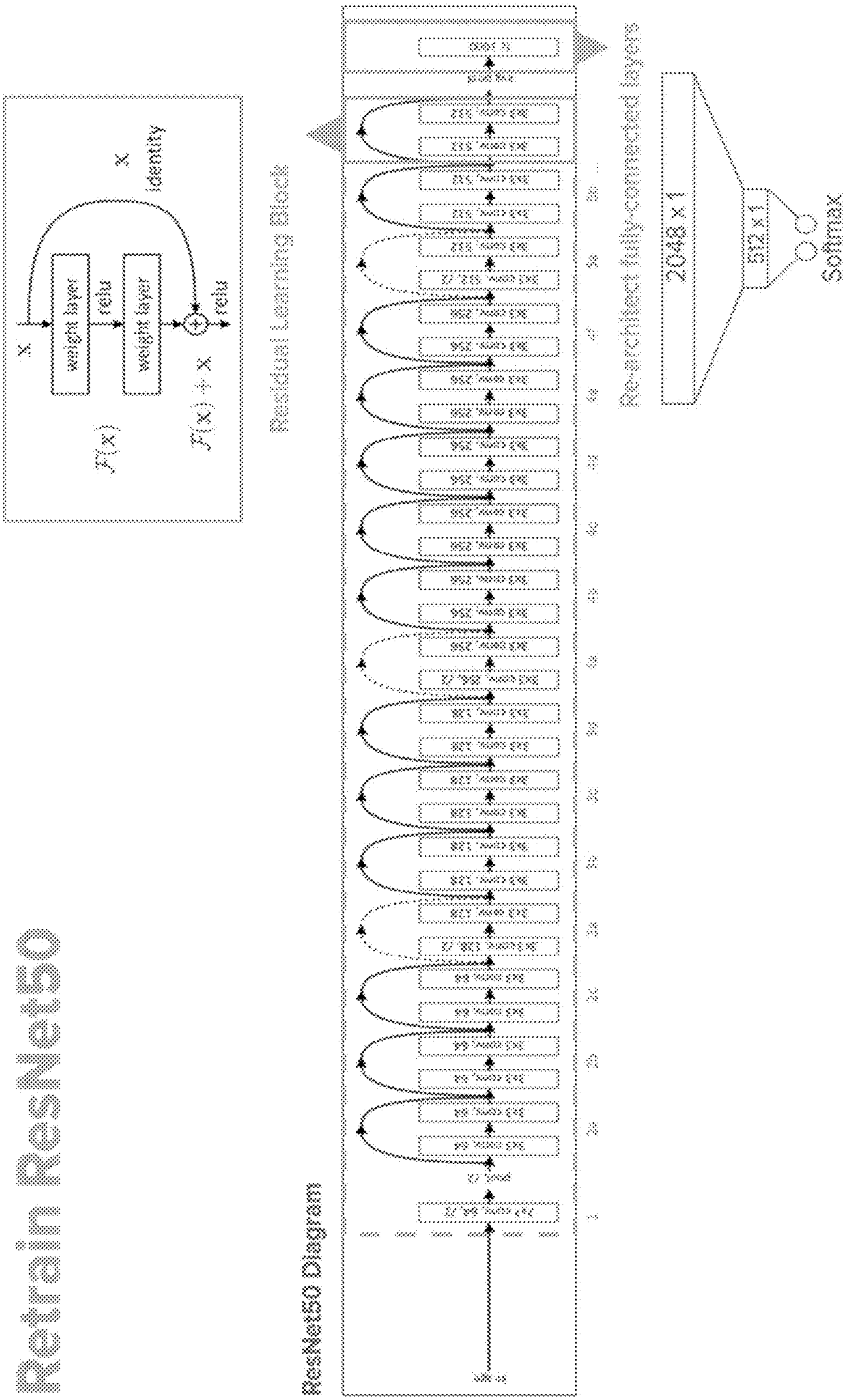

Referring to FIG. 18, the network that achieved this result had the following structure: a ResNet50 model that takes the masks as inputs of dimensions (762, 787, 3), and is cut at "activation_40" layer. The "activation_40" layer of ResNet50 is found at the end of block 4f in Resnet50 architecture.

The output of this block 4f is then followed by a global average pooling layer which provides a vector of size 1024. This vector is inputted to two dense layers of units respectively 520 and 10, outputting a vector of size 10. This vector is concatenated to the clinical and genomic data vector of size 10 each, providing a vector of size 30. This vector is then inputted to a dense layer of units 16 and then to the last dense layer which outputs the risk score.

Due to the size of ResNet50, no complete graphical representation of this network is provided for the sake of concision.

Several options were tested based on ResNet50, either using the entire model, cutting it after block 4f, or after block 3d. Cutting the network early allows to use low-level features.

Ensemble models were also tested which had a maximum concordance index of 0.6703. The network that achieved this result had the following structure: with the three masks stacked as channels, the visual input dimensions are (700, 700, 3). This input is inputted to five convolutional and pooling layers of kernel size (5,5) and pool size (2,2). The convolutional units are 16, then 24, then 32, then 40, and then 48. A global average pooling is then applied, providing a vector of size 48. Two dense layers are then applied, which transform this vector into a vector of size 32, and then 24. A final dense layer outputs a scalar (the risk score). For the clinical data of size 10, only one dense layer is applied, outputting a risk score. For the genomic data of size 10, a first dense layer is applied, outputting a vector of size 5, and then a final dense layer is applied to output the risk score. The three risk scores are then concatenated, to make a vector of size 3, and inputted to a last dense layer which outputs the final risk score.

Figure 19:
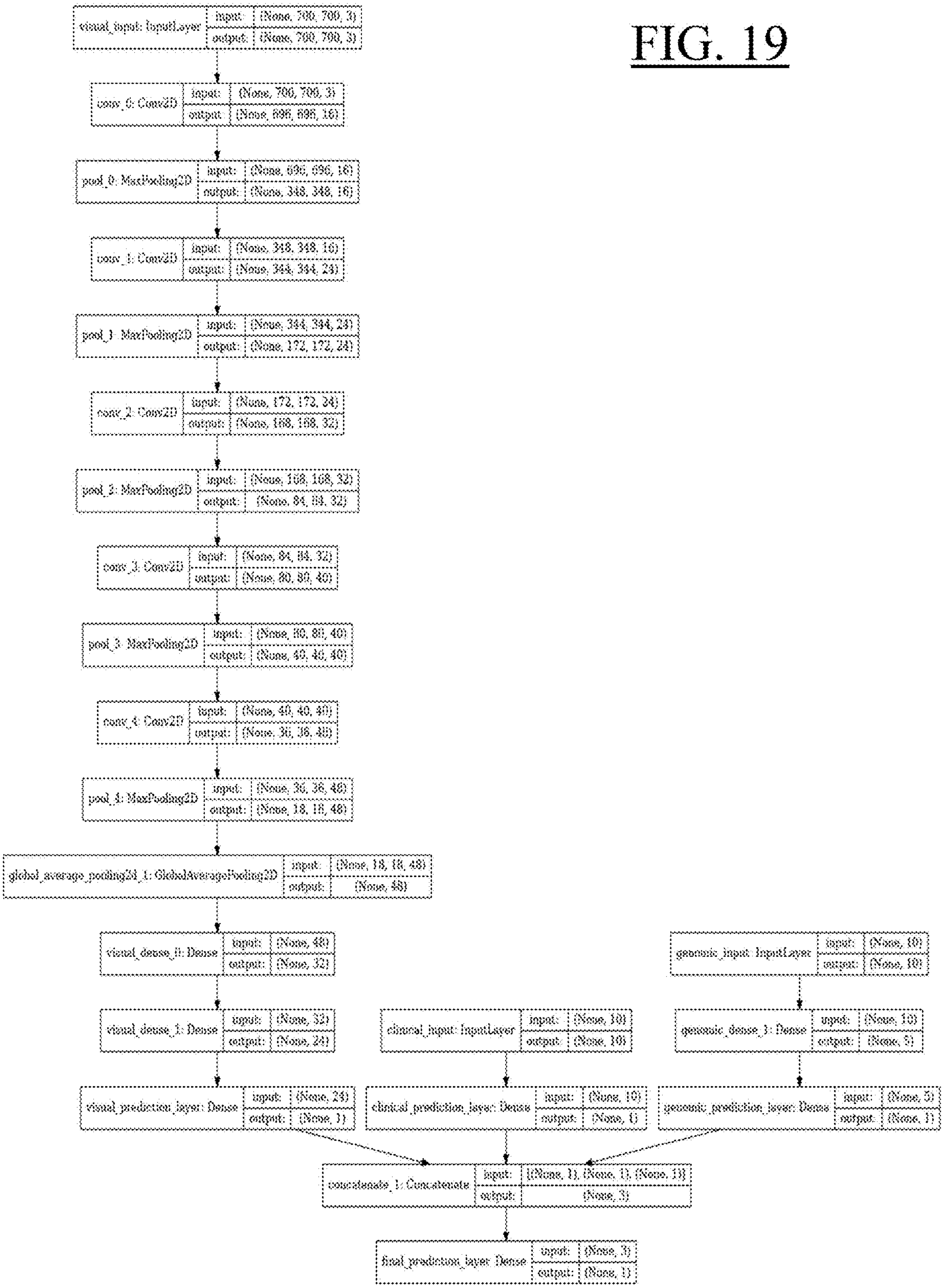

FIG. 19 shows the structure of this network:

For each of these models, a random hyperparameter search was performed to find hyperparameters as optimal as possible (number of convolutional layers, number of dense layers, number of units, etc.). Most times, the units had to be kept low not to overflow memory usage.

In variations of the presented models, the masks may be provided either as individual images to three CNNs, or stacked as one image with three channels (one corresponding to the textures mask, one to the lymphocytes mask, and one to the cells mask) to one CNN. The masks may also be either resized to dimensions (700,700) or padded with background to reach the size of (762,787), which was the size of the largest mask in the dataset.

The following table summarizes the obtained results:

| Deep Learning Models | Concordant index |
|---|---|
| ResNet transfer learning + NN (parameters: {'encoding': 0, 'lr': 0.001, 'n_layers_1': 1, 'n_layers_2': 1, 'stop_layers': 1, 'units': 10}) | 0.6792 +/− 0.083 |
| Simple CNN + NN [3 channels] (parameters: {'encoding': 0, 'filters': (8, 56), 'kernel_size': (5, 5), 'lr': 0.001, 'n_conv_layers': 3, 'n_dense_layers': 1, 'pool_size': (2, 2), 'units': 100}) | 0.6750 +/− 0.084 |
| Simple CNN + NN [separate masks], padding (parameters: {'encoding': 0, 'filters': (8, 56), 'kernel_size': (5, 5), 'lr': 0.0001, 'n_conv_layers': 4, 'n_dense_layers': 1, 'pool_size': (2, 2), 'units': 1000}) | 0.6809 +/− 0.102 |
| Autoencoder features extraction + NN [3 channels] (parameters: {'encoding': 0, 'lr': 0.0001, 'n_dense_layers': 1, 'units': 2000}) | 0.6736 +/− 0.076 |
| Ensemble model (Simple CNN and NNs, learning as goes) [3 channels] (parameters: {'clinical_dense_layers': 0, 'filters': (8, 56), 'genomic_dense_layers': 1, 'kernel_size': (5, 5), 'lr': 0.01, 'n_conv_layers': 5, 'pool_size': (2, 2), 'units': 5, 'visual_dense_layers': 2}) | 0.6703 +/− 0.084 |

The invention claimed is:

1. A computer-implemented method for parameterizing a statistical function configured for performing prognosis on cancer patients to modulate treatment based on the prognosis, the method comprising:

obtaining a dataset relative to a plurality of patients each having a cancer disease, the dataset including for each patient:

input data of the statistical function, the input data including:

visual data from at least one histological image of a tumor slide of the patient, wherein the visual data are obtained from at least three maps including:

a texture map extracted from the at least one histological image via a first CNN, the texture map having pixels each representing a texture among a predetermined set of textures, the set of textures representing at least two among adipose, background, debris, lymphocytes, mucus, muscle, normal mucosa, stroma, and tumor, each pixel resulting from classifying a respective tile of the at least one histological image with the first CNN, a lymphocyte map extracted from the at least one histological image via a second CNN, the lymphocyte map having pixels each indicative of lymphocyte presence, each pixel resulting from classifying a respective tile of the at least one histological image with the second CNN, and a cell density map extracted from the at least one histological image via a third CNN, the cell density map having a plurality of pixels each representing a local number of cells, each pixel resulting from counting a number of cells in a respective and different tile of the at least one histological image with the third CNN, genomic data from sequencing tumor tissue of the patient, and clinical data of the patient, obtaining clinical endpoints of the patient with respect to evolution of the cancer disease; and parameterizing the statistical function based on the dataset, the statistical function being thereby configured for performance of prognosis on cancer patients to modulate treatment based on the prognosis.

2. The computer-implemented method of claim 1, wherein the genomic data represent a cell-type distribution and/or gene expression data.

3. The computer-implemented method of claim 1, wherein the clinical data represent at least one among patient age, patient gender, tumor stage, lymph node stage and/or metastasis stage.

4. The computer-implemented method of claim 1, wherein the statistical function comprises a neural network, a stochastic model, and/or a regression model such as a Cox model.

5. The computer-implemented method of claim 1, wherein the statistical function is configured to output a prediction on patient's outcome and/or a prediction on tumor evolution.

6. A method of implementing a statistical function for performing prognosis on a cancer patient to modulate treatment based on the prognosis, the statistical function being parameterized by parameterizing a statistical function configured to perform prognosis on cancer patients to modulate treatment based on the prognosis, the method comprising:

capturing at least one histological image of a tumor slide of a patient:

extracting from the at least one histological image:

a texture map extracted from the at least one histological image via a first CNN, the texture map having pixels each representing a texture among a predetermined set of textures, the set of textures representing at least two among adipose. background, debris, lymphocytes, mucus, muscle, normal mucosa. stroma. and tumor, each pixel resulting from classifying a respective tile of the at least one histological image with the first CNN, a lymphocyte map extracted from the at least one histological image via a second CNN, the lymphocyte map having pixels each indicative of lymphocyte presence, each pixel resulting from classifying a respective tile of the at least one histological image with the second CNN, and a cell density map extracted from the at least one histological image via a third CNN, the cell density map having a plurality of pixels each representing a local number of cells, each pixel resulting from counting a number of cells in a respective and different tile of the at least one histological image with the third CNN, obtaining input data including:

visual data as a function of the texture map, the lymphocyte map, and the cell density map, genomic data from sequencing tumor tissue of the patient, and clinical data of the patient; and applying the parametrized statistical function to the input data to perform prognosis on the patient, thereby outputting a prediction on patient's outcome and/or a prediction on tumor evolution; and modulating treatment of the patient based on the outputted prediction.

7. The method of claim 6, wherein the statistical function comprises a neural network comprising:

one or more convolutional layers to process at least three maps and provide one or more intermediate outputs;

one or more pooling layers to process each intermediate output and provide a respective vector per intermediate output; and one or more fully connected layers configured to process a global vector formed by concatenating genomic and clinical data, each in the form of a respective numeric vector, with feature vectors, and to output the prediction on the patient's outcome and/or the prediction on tumor evolution.

8. The method of claim 6, further comprising displaying information based on the outputted prediction and input data on a graphical user interface.

9. The method of claim 6, wherein the modulation includes at least one of:

therapy nature or intensity, follow-up scheduling with surveillance tests, and optimal treatment recommendation for the patient.

10. A device comprising:

a non-transitory computer-readable data storage medium having recorded thereon a computer program having instructions, that when executed by a processor causes the processor to be configured to at least one of:

i) parameterize a statistical function configured for performing prognosis on cancer patients to modulate treatment based on the prognosis by the processor being configured to:

obtain a dataset relative to a plurality of patients each having a cancer disease, the dataset including for each patient:

input data of the statistical function, the input data including:

visual data from at least one histological image of a tumor slide of the patient, wherein the visual data are obtained from at least three maps including:

a texture map extracted from the at least one histological image via a first CNN, the texture map having pixels each representing a texture among a predetermined set of textures, the set of textures representing at least two among adipose, background, debris, lymphocytes, mucus, muscle, normal mucosa, stroma, and tumor, each pixel resulting from classifying a respective tile of the at least one histological image with the first CNN, a lymphocyte map extracted from the at least one histological image via a second CNN, the lymphocyte map having pixels each indicative of lymphocyte presence, each pixel resulting from classifying a respective tile of the at least one histological image with the second CNN, and a cell density map extracted from the at least one histological image via a third CNN, the cell density map having a plurality of pixels each representing a local number of cells, each pixel resulting from counting a number of cells in a respective and different tile of the at least one histological image with the third CNN, genomic data from sequencing tumor tissue of the patient, and clinical data of the patient, and obtain clinical endpoints of the patient with respect to evolution of the cancer disease; and parameterize the statistical function based on the dataset, the statistical function being thereby configured for performance of the prognosis on cancer patients to modulate treatment based on the prognosis; and ii) implement a statistical function for performing prognosis on a cancer patient to modulate treatment based on the prognosis, the statistical function being parameterized by parameterizing a statistical function configured for performance of prognosis on cancer patients to modulate treatment based on the prognosis by the processor being configured to:

capture at least one histological image of a tumor slide of a patient;

extract from the at least one histological image:

a texture map extracted from the at least one histological image via a first CNN, the texture map having pixels each representing a texture among a predetermined set of textures, the set of textures representing at least two among adipose, background, debris, lymphocytes, mucus, muscle, normal mucosa, stroma, and tumor, each pixel resulting from classifying a respective tile of the at least one histological image with the first CNN, a lymphocyte map extracted from the at least one histological image via a second CNN. the lymphocyte map having pixels each indicative of lymphocyte presence, each pixel resulting from classifying a respective tile of the at least one histological image with the second CNN, and a cell density map extracted from the at least one histological image via a third CNN, the cell density map having a plurality of pixels each representing a local number of cells, each pixel resulting from counting a number of cells in a respective and different tile of the at least one histological image with the third CNN, obtain input data including:

visual data as function of the texture map, the lymphocyte map, and the cell density map, genomic data from sequencing tumor tissue of the patient, and clinical data of the patient;

apply the parametrized statistical function to the input data to perform prognosis on the patient, thereby outputting a prediction on patient's outcome and/or a prediction on tumor evolution; and modulate treatment of the patient based on the outputted prediction.

11. The device of claim 10, wherein the device further comprises the processor coupled to the non-transitory computer-readable data storage medium.

12. A non-transitory computer readable medium having stored thereon a program that when executed by a computer causes the computer to implement the method for parameterizing the statistical function configured for performing prognosis on cancer patients according to claim 1.

13. A non-transitory computer readable medium having stored thereon a program that when executed by a computer causes the computer to implement the method for implementing the statistical function for performing prognosis on the cancer patient according to claim 6.

* * * * *